US012674142B2

(12) United States Patent
Heilshorn et al.

(10) Patent No.: US 12,674,142 B2
(45) Date of Patent: Jul. 7, 2026

(54) HYDROGEL COMPOSITIONS AND METHODS OF USE THEREOF

(71) Applicant: The Board of Trustees of the Leland Stanford Junior University, Stanford, CA (US)

(72) Inventors: Sarah Heilshorn, Mountain View, CA (US); Riley Suhar, Redwood City, CA (US); Daniel Hunt, Redwood City, CA (US)

(73) Assignee: The Board of Trustees of the Leland Stanford Junior University, Stanford, CA (US)

( * ) Notice: Subject to any disclaimer, the term of this patent is extended or adjusted under 35 U.S.C. 154(b) by 531 days.

(21) Appl. No.: 18/033,536

(22) PCT Filed: Nov. 3, 2021

(86) PCT No.: PCT/US2021/057925
§ 371 (c)(1),
(2) Date: Apr. 24, 2023

(87) PCT Pub. No.: WO2022/098777
PCT Pub. Date: May 12, 2022

(65) Prior Publication Data

US 2023/0365940 A1 Nov. 16, 2023

Related U.S. Application Data

(60) Provisional application No. 63/110,667, filed on Nov. 6, 2020.

(51) Int. Cl.
*C12N 5/071* (2010.01)
*C12N 5/00* (2006.01)

(52) U.S. Cl.
CPC ......... *C12N 5/0679* (2013.01); *C12N 5/0012* (2013.01); *C12N 2509/00* (2013.01);
(Continued)

(58) Field of Classification Search
CPC ................ C12N 5/0679; C12N 5/0012; C12N 2509/00; C12N 2513/00; C12N 2533/50;
(Continued)

(56) References Cited

U.S. PATENT DOCUMENTS

2020/0038484 A1 2/2020 Myung et al.

OTHER PUBLICATIONS

Caliari, Steven R., and Jason A. Burdick. "A practical guide to hydrogels for cell culture." Nature methods 13.5 (2016): 405-414 (Year: 2016).*

(Continued)

*Primary Examiner* — Tracy Vivlemore
*Assistant Examiner* — Thomas R. Amick
(74) *Attorney, Agent, or Firm* — Bozicevic, Field & Francis LLP; Andrew R. Guzman; Pamela J. Sherwood

(57) ABSTRACT

A two-component hydrogel matrix system is provided, which system is useful in a variety of cell growth uses, including without limitation three-dimensional culture systems. The components comprise modified hyaluronic acid (HA); and modified elastin-like proteins (ELP). Variables of HELP, including for example, matrix stiffness, matrix stress relaxation rate, and cell-adhesive-ligand concentration, can be independently and quantitatively specified.

20 Claims, 15 Drawing Sheets

Specification includes a Sequence Listing.

(52) U.S. Cl.
CPC ...... *C12N 2513/00* (2013.01); *C12N 2533/50* (2013.01); *C12N 2533/80* (2013.01); *C12N 2537/10* (2013.01)

(58) Field of Classification Search
CPC ............ C12N 2533/80; C12N 2537/10; C12N 2501/905; C12N 2501/998; C12N 5/0068; C12N 5/0062
See application file for complete search history.

(56) References Cited

OTHER PUBLICATIONS

Lampe, Kyle J., Alexander L. Antaris, and Sarah C. Heilshorn. "Design of three-dimensional engineered protein hydrogels for tailored control of neurite growth." Acta biomaterialia 9.3 (2013): 5590-5599 (Year: 2013).*

Lou, Junzhe, et al. "Stress relaxing hyaluronic acid-collagen hydrogels promote cell spreading, fiber remodeling, and focal adhesion formation in 3D cell culture." Biomaterials 154 (2018): 213-222 (Year: 2018).*

Richardson, Benjamin M., et al. "Hydrazone covalent adaptable networks modulate extracellular matrix deposition for cartilage tissue engineering." Acta biomaterialia 83 (2019): 71-82 (Year: 2019).*

Zhu, Danqing, et al. "Elastin-like protein-hyaluronic acid (ELP-HA) hydrogels with decoupled mechanical and biochemical cues for cartilage regeneration." Biomaterials 127 (2017): 132-140) (Provided in IDS of Apr. 24, 2023 (Year: 2017).*

Wang et al. (2017) "Covalently adaptable elastin-like protein-hyaluronic acid (ELP-HA) hybrid hydrogels with secondary thermoresponsive crosslinking for injectable stem cell delivery". *Advanced functional materials*, 27(28), pp. 1-11, 1605609.

Zhu et al. (2017) "Elastin-like Protein-Hyaluronic acid (ELP-HA) Hydrogels with Decoupled Mechanical and Biochemical cues for Cartilage Regeneration," Biomaterials. vol. 127, pp. 132-140.

Krishna et al.(2012) "Hydrazone Self-Crosslinking of Multiphase Elastin-Like Block Copolymer 1-3 Networks." Acta BiomaiArialia. vol. 8, Issue 3, pp. 988-997.

Suhar et al. (2021) "Hyaluronan and Elastin-Like Protein (HELP) Gels Significantly Improve Cargo 1-3,., Retention in the Myocardium,".

* cited by examiner

| | |
|---|---|
| RGD | 33-34 |
| RDG | 33-34 |
| YIGSR | 47-48 |
| IKVAV | 54-55 |
| DGEA | 48-49 |
| PLAEIDGIELTY | 44-45 |
| VDFNVL | 44-45 |
| VDFNVLK | 35-36 |
| HAVDI | 39-40 |
| HAVDINGHAVDI | 41-42 |
| ADHIV | 40-41 |

from top to bottom SEQ ID NOs:31, 32, 7, 6, 3, 4, 26, 27, 8, 28, 29 from top to bottom SEQ ID NOs:31, 32, 7, 6, 3, 4, 26, 27, 8, 28, 29 from top to bottom SEQ ID NOs:31, 7, 3, 4, 33, 32 from top to bottom SEQ ID NOs:31, 7, 3, 4, 26, 32

A

| Injection Criterion |
|---|
| *1. Injectable after complete gelation.* |
| *2. Injectable with one hand through a 30-G needle.* |
| *3. Must have no "burst" injection.* |

B

C

| Injection Scording | | | |
|---|---|---|---|
| **HA-Variant** | **1** | **2** | **3** |
| *HA24* | ✓ | ✓ | ✓ |
| *HA16* | ✓ | ✓ | ✓ |
| *HA8* | ✓ | ✗ | ✗ |
| *HA-A* | ✓ | ✗ | ✗ |
| *HA-B* | ✗ | - | - |

HYDROGEL COMPOSITIONS AND METHODS OF USE THEREOF

CROSS REFERENCE TO RELATED APPLICATION

The present application claims the benefit of and priority to U.S. Provisional Patent Application No. 63/110,667, filed Nov. 6, 2020, the entire disclosure of which is hereby.

INCORPORATION BY REFERENCE OF SEQUENCE LISTING PROVIDED AS A TEXT FILE

A Sequence Listing is provided herewith in a text file, (STAN-1763WO_SEQ_LIST_ST25.txt), created on Nov. 3, 2021, and having a size of 21000 bytes. The contents of the text file are incorporated herein by reference in its entirety.

BACKGROUND

Human tissues, including human organoids derived from primary tissue of patient biopsies or pluripotent cells have the potential to revolutionize personalized medicine and preclinical models of disease. However, human patient-derived organoids in synthetic matrices have often required either a spheroid formation step, e.g. in decellularized Engelbreth-Holm-Swarm (EHS) matrix or co-culture with feeder cells.

Recent work to develop engineered matrices for patient-derived organoids have relied on polyethylene glycol (PEG) as a synthetic matrix backbone, although PEG is known to interact with the immune system and induce antibody formation.

A reproducible, biodegradable, minimal matrix with no animal-derived products or synthetic PEG is of great interest for clinical translation, and is addressed by the disclosure herein.

SUMMARY

A two-component hydrogel matrix system is described, which has a variety of benefits for cell and tissue culture; including without limitation the provision of a three-dimensional culture environment. The components comprise: (1) chemically modified hyaluronic acid (HA), and (2) chemically modified elastin-like protein (ELP). Mixing the two modified biopolymers together induces the formation of hydrazone bonds resulting in a hydrogel network, referred to herein as “HELP”. Selection of the ratio between HA and ELP, and the ratio of variants of these components allows tuning of critical variables of HELP, including, for example, matrix stiffness, matrix stress relaxation rate, and cell-adhesive-ligand concentration and identity. These variables can be independently and quantitatively defined.

The hyaluronic acid component is chemically modified to comprise a pendant benzaldehyde or aldehyde side group. The specific ratio of these two chemical groups in the final hydrogel formulation controls the stress relaxation variable. A key feature of native extracellular matrices and EHS matrices is their ability to undergo stress relaxation due to their physical crosslinks, which can be easily remodeled. Compositions comprising a greater percentage of hyaluronic acid modified with a pendant aldehyde group, increase the average kinetic exchange rate of the gel, leading to a faster stress-relaxation rate. A greater percentage of hyaluronic acid modified with a pendant benzaldehyde group decreases the average kinetic exchange rate of the gel, leading to slower stress-relaxation rate. Modifications to stress-relaxation rate can be achieved independently of matrix ligand composition and stiffness. The ratio of HA-benzaldehyde to HA-aldehyde may be pre-selected for a hydrogel of interest, usually ranging from about 100:0 to 0:100, for example at a ratio from about 95:5, 90:10, 75:25, 50:50, 25:75, etc.

The ELP component comprises a recombinant sequence of elastin-like sequences optionally interspersed with cell-adhesive sequences. To engage in crosslinking with chemically modified HA, the ELP is chemically modified to comprise a pendant hydrazine group. The optional cell-adhesive sequence within the ELP may be selected from an integrin-binding, fibronectin-based, extended RGD sequence, a scrambled RGD sequence, a cell-adhesive sequence derived from collagen type I, e.g. (SEQ ID NO:3) DGEA, a cell adhesive sequence derived from tenascin, e.g. (SEQ ID NO:4) PLAEIDGIELTY, (SEQ ID NO:5) VFDNFVLK, etc.; a cell adhesive sequence derived from laminin, e.g. (SEQ ID NO:6) IKVAV, (SEQ ID NO:7) YIGSR, etc.; a cell adhesive sequence derived from cadherin, e.g. (SEQ ID NO:8) HAVDI, (SEQ ID NO:9) HAVDIHAVDI; and the like. For example, SEQ ID NO:1 and SEQ ID NO:2 are ELPs with an RGD sequence, and a scrambled RGD sequence, respectively.

The cell-adhesive sequence concentration of the hydrogel can be varied by adjusting the ratio of ELP comprising an RGD motif, to ELP lacking an RGD motif or comprising scrambled or non-RGD cell-adhesive motifs, as disclosed above. The ratio may be pre-selected for a hydrogel of interest, usually ranging from about 100:0 to 0:100, for example from about 75:25, 50:50, 25:75, 10:90. For some applications, a HELP hydrogel comprises from about 0.25 mM RGD up to about 1.5 mM RGD, e.g. about 0.25 mM, 0.5 mM, 0.75 mM, 1 mM, 1.25 mM, 1.5 mM. Greater than 0.75 mM is preferred for culture of intestinal organoids.

Matrix stiffness is determined by the concentration and ratio of hydrazine to aldehyde and benzaldehyde reactive groups, where a ratio of about 1:1 provides for maximum cross-linking. The ratio may be varied, e.g. from about 1:3, about 1:2, about 1.5:1, about 1.25:1, about 1:1, about 1:1.25, about 1:1.5, about 1:2, about 1:3, etc. For cell culture purposes, a preferred gel may have a G' of about 1 kPa, e.g. from about 750 to 1250 Pa. The ratio of hydrazine to aldehyde or benzaldehyde groups can be altered through three variables: (1) number of hydrazine groups per ELP molecule, (2) number of aldehyde or benzaldehyde groups per HA molecule, and (3) the blending of ELP and HA.

In some embodiments, a hydrogel matrix as disclosed herein is used in the culture of cells in vitro. In some embodiments a 3D culture environment is provided comprising a matrix of a tunable HELP hydrogel. In some embodiments a method of culturing mammalian cells in vitro is provided, the method being comprised of suspending a cell population of interest, which may be primary cells, cell lines, in vitro reprogrammed cells, genetically modified cells, primary tissue explants, etc., in a hydrogel as described herein, and culturing the embedded cells in a suitable medium. In some embodiments the cells are primary cells from a human patient. In some embodiments the culture system is free of polyethylene glycol.

In some embodiments, cells cultured in a hydrogel matrix, as disclosed herein, differentiate into cells of a tissue of interest. For example, intestinal stem cells or intestinal explants can be differentiated into intestinal organoids; etc. The cells additionally may be passaged by a process of matrix dissociation. In matrix dissociation, the HELP matrices can be enzymatically degraded using elastase and hyaluronidase. Formed organoids can be dissociated further into single cells or small cell aggregates, e.g. with trypsin, or can be passaged intact. Encapsulation of single cells or small cell aggregates into fresh HELP matrix provides for successive organoid formation for at least 12 passages without visible change in morphology. Alternatively, cells can be pre-formed into spheroids and then encapsulated within the HELP matrix.

Tissues include but are not limited to intestinal tissue, lung tissue, stomach tissue, pancreatic tissue, bladder tissue, liver tissue, bone marrow stroma, muscle tissue, kidney tissue, brain tissue, etc. Cultured explants of the invention can be continuously grown in culture for periods of time, for example for 1 week, 2 weeks, 3 weeks, 4 weeks, or more. Mammalian tissue explants cultured by the methods of the invention can recapitulate features of tissue growth in vivo. Features include, without limitation, prolonged tissue expansion with proliferation, multilineage differentiation, and recapitulation of cellular and tissue ultrastructure, including epithelial tissues, submucosal tissues, and stromal environments, While the culture system provides for growth of the varied cells found in normal or diseased mammalian tissues, the cultures are also useful in the generation of cells for selection, to provide purified populations or enriched populations of a single lineage for any given tissue, including tissue-specific stem cells. Organoids cultured by these methods find use in many applications such as tissue engineering, disease modeling, and drug discovery.

The cultured cells may be experimentally modified prior to or during the culture period. In some embodiments, the cells are modified by exposure to viral or bacterial pathogens. In other embodiments, the cells are modified by altering patterns of gene expression, e.g. by providing reprogramming factors to induce pluripotency or otherwise alter differentiation potential, or by introducing cancer drivers that provide for oncogenic transformation of cells into carcinomas, etc. The experimentally modified cells are useful for investigation of the effects of therapeutic agents; for tumor therapy, for effects on differentiation, and the like.

Methods are provided for screening cells in a population, e.g. a complex population of multiple cell types, a population of purified cells isolated from a complex population by sorting, culture, etc., and the like, for the presence of cells having stem cell potential. This method entails co-culture of detectably labeled candidate cells with the tissue explant of the invention. Candidate cells with stem cell potential are detected by an increase in growth of the cultured explant above basal levels and colocalization of multilineage differentiation markers indicative of the presence of tissue-specific stem cells with the labeled candidate cells. Stem cell characteristics of candidate cells co-cultured with explants are further assayed by determining long-term reconstitutive activity, via in vivo transplantation, etc.

In another aspect of the invention, a method is provided for in vitro screening of agents for cytotoxicity to different tissues, by screening for toxicity to explant cultures of the invention. In yet another embodiment, a method is provided to assess drug absorption by different tissues, by assessing absorption of a drug by explant cultures of the invention.

In another aspect of the invention, the matrix is extruded through a syringe needle or a catheter. After extrusion, the HELP matrix reforms a gel-phase material. Cells encapsulated within the HELP matrix can be extruded in this manner for use as a bio-ink for 3D bioprinting; for injectable regenerative medicine therapy; etc. A shear-thinning material with a fracture stress below 2,000 Pa is injectable by hand force. The fracture stress can be adjusted by changing three variables: (1) the molecular weight of the HA, usually with MW below 100 kDa, (2) the kinetics of the hydrazone bond, with the fast exchange kinetics of the hydrazine-aldehyde preferred over the slower exchange kinetics of the hydrazine-benzaldehyde reaction for this purpose, and (3) the overall polymer concentration, usually with a final concentration of from about 0.5-2 wt % of ELP and from about 0.5-2 wt % of HA.

DETAILED DESCRIPTION

Definitions

Figure 1:
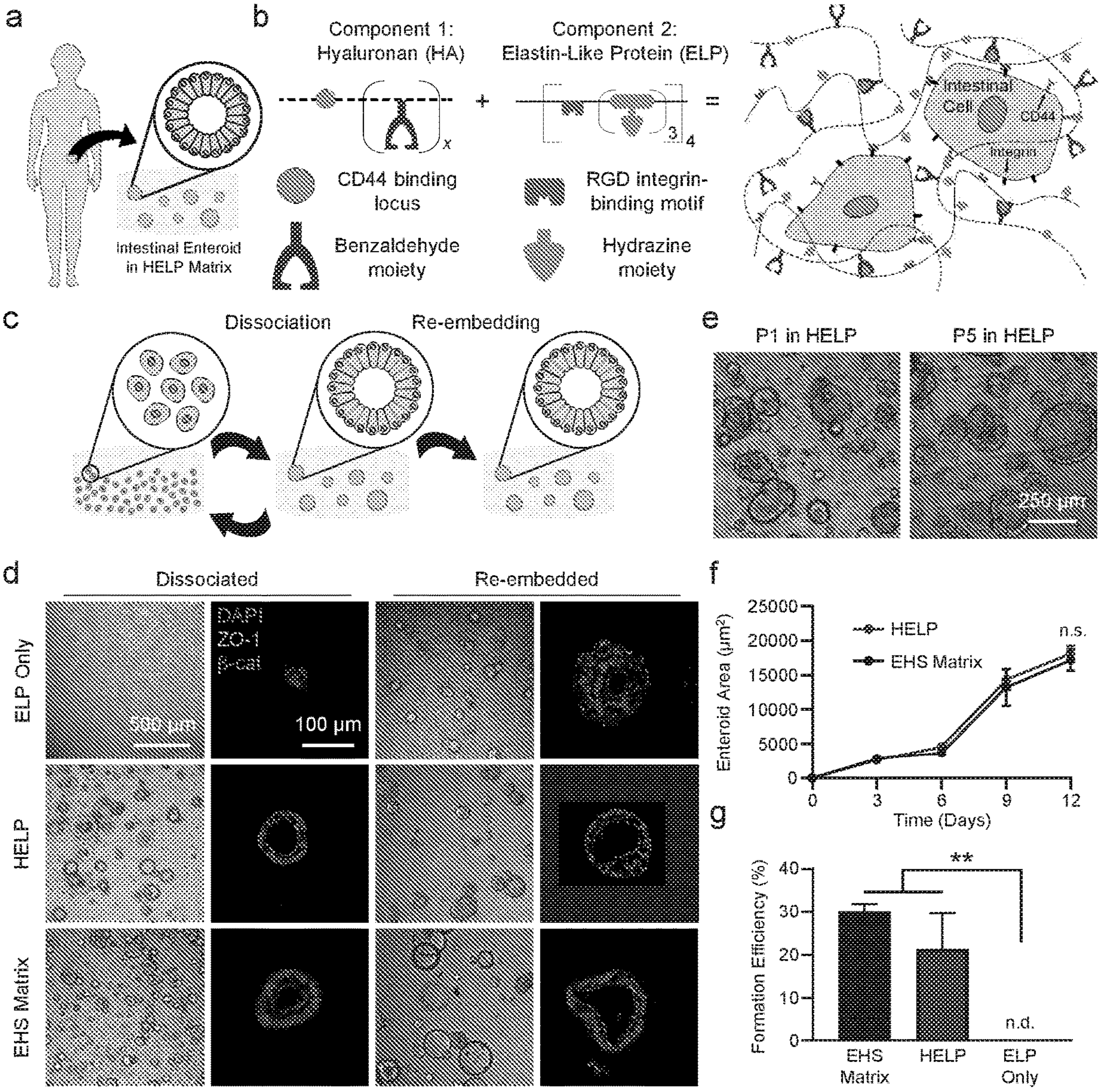
FIG. 1: HELP matrix for patient-derived intestinal organoid formation, growth, and passaging. a) Enteroids were generated from intestinal tissue biopsies from human patients. b) Schematic of HELP matrix, which is composed of benzaldehyde-modified hyaluronan (HA) and hydrazine-modified elastin-like protein (ELP). Hyaluronan can engage the CD44 receptors on cells, while recombinant ELP contains an RGD peptide ligand that engages cell integrin receptors. c) Schematic of enteroid passaging techniques. Enteroids can either be dissociated into single cells or directly re-embedded as fully formed enteroids into a new material at the time of passaging. d) Brightfield and confocal fluorescence micrographs of enteroids in different materials, when dissociated (left) and re-embedded (right) in these materials. e) Representative brightfield images of enteroids grown on Passage 1 and Passage 5 in HELP, with dissociation into single cells at the time of each passage. f) Growth curves of dissociated enteroids grown from Passage 12 in EHS matrix or Passage 12 in HELP; n=3, n.s.=not significant. g) Enteroid formation efficiency for enteroids grown from single cells in the material formulations shown in d). Data are mean+/−standard deviation, 1-way ANOVA with Tukey's multiple comparisons testing; **=$p<0.01$, n=3, n.d.=none detected.

Before embodiments of the present disclosure are further described, it is to be understood that this disclosure is not limited to particular embodiments described, as such may, of course, vary. It is also to be understood that the terminology used herein is for the purpose of describing particular embodiments only, and is not intended to be limiting, since the scope of the present disclosure will be limited only by the appended claims.

Unless defined otherwise, all technical and scientific terms used herein have the same meaning as commonly understood by one of ordinary skill in the art to which this disclosure belongs. Any methods and materials similar or equivalent to those described herein can also be used in the practice or testing of embodiments of the present disclosure.

It must be noted that as used herein and in the appended claims, the singular forms "a", "and", and "the" include plural referents unless the context clearly dictates otherwise.

Thus, for example, reference to “a compound” includes not only a single compound but also a combination of two or more compounds, reference to “a substituent” includes a single substituent as well as two or more substituents, and the like.

In describing and claiming the present invention, certain terminology will be used in accordance with the definitions set out below. It will be appreciated that the definitions provided herein are not intended to be mutually exclusive. Accordingly, some chemical moieties may fall within the definition of more than one term.

As used herein, the phrases “for example,” “for instance,” “such as,” or “including” are meant to introduce examples that further clarify more general subject matter. These examples are provided only as an aid for understanding the disclosure, and are not meant to be limiting in any fashion.

The term “hydrogel” is used in its conventional sense to refer to a material that absorbs a solvent (e.g. water), undergoes swelling without measurable dissolution, and maintains three-dimensional networks capable of reversible deformation. “Swelling” as referred to herein is meant the isotropic expansion of the hydrogel structure as water molecules diffuse throughout the internal volume of the hydrogel. The properties of copolymer hydrogels disclosed herein may be modulated as desired, by varying the amounts of each component, ratios of each component or the density of specific components, as described in greater detail below. The term hydrogel may include both desiccated and hydrated (e.g., solvent swollen) hydrogels.

In some embodiments of the invention the hydrogel provides a scaffold for cell growth, including growth of metabolically active cells, e.g. differentiating cells, etc. The cells may be grown in vitro, e.g. a culture of one or a plurality of cell types. Cells may also be grown in vivo, e.g. where a hydrogel provides a substrate for regenerative cell growth. The hydrogels of the invention provide appropriate mechanical strength for long term structural stability.

An Elastin-like Protein (ELP) comprises a recombinant sequence of elastin-like sequences optionally interspersed with cell-adhesive sequences. To engage in crosslinking with chemically modified HA, the ELP is chemically modified to comprise a pendant hydrazine group. The optional cell-adhesive sequence within the ELP comprises a motif involved in cell adhesion, which may be selected from an integrin-binding, fibronectin-based, extended RGD sequence, a scrambled RGD sequence, a cell-adhesive sequence derived from collagen type I, e.g. (SEQ ID NO:3) DGEA, a cell adhesive sequence derived from tenascin, e.g. (SEQ ID NO:4) PLAEIDGIELTY, (SEQ ID NO:5) VFDNFVLK, etc.; a cell adhesive sequence derived from laminin, e.g. (SEQ ID NO:6) IKVAV, (SEQ ID NO:7) YIGSR, etc.; a cell adhesive sequence derived from cadherin, e.g. (SEQ ID NO:8) HAVDI, (SEQ ID NO:9) HAVDIHAVDI; and the like.

The cell-adhesive domain of the engineered elastin-like protein can be designed to include alternative peptide-sequences known to interact with cell-surface receptors. These sequences can include peptides derived from native extracellular matrix proteins (e.g. fibronectin, laminin, collagen, tenascin-C) or peptides derived from cell-cell adhesion receptors (e.g. N-cadherin) (Table 1). Selection of the cell adhesive peptide sequence together with the elastin-like region sequence defines the overall hydrophobicity of the engineered protein, and hence controls the lower critical solution temperature (LOST) behavior.

In some embodiments an ELP comprises the structure:

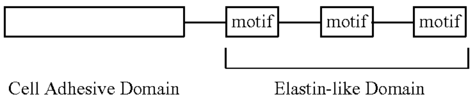

where the cell adhesive domain is from about 15 to about 45 amino acids in length and comprises one or more cell adhesion sequence motifs, which may be selected from RGD, scrambled RGD, no RGD, or any of SEQ ID NO:3 to SEQ ID NO:9. SEQ ID NO:10-19 and 22 are exemplary.

Linker sequences optionally flank the cell adhesion sequence motif, where a peptide linker can be between about 5 to 20, 5 to 15, 5 to 10 or 5 to 9 amino acids in length. Exemplary linkers include linear peptides having at least two amino acid residues such as Gly-Gly, Gly-Ala-Gly, Gly-Pro-Ala, Gly-Gly-Gly-Gly-Ser (SEQ ID NO:34). Suitable linear peptides include poly glycine, polyserine, polyproline, polyalanine and oligopeptides consisting of alanyl and/or serinyl and/or prolinyl and/or glycyl amino acid residues. In one embodiment a linker comprises the amino acid sequence GSTSGSGKSSEGKG (SEQ ID NO:35), or (GGGGS)n (SEQ ID NO:36), where n is 1, 2, 3, 4, 5, etc.; however many such linkers are known and used in the art and may serve this purpose.

The elastin-like domain is comprised of elastin-like motifs, which include, without limitation, (SEQ ID NO:23) VPGIG; (SEQ ID NO:24) VPGKG; (SEQ ID NO:25) VPGYG. One or more of SEQ ID NO:23, 24 and 25 can be present in a protein. In some embodiments the number of motifs is from 1 to 7, from 1 to 6, from 2 to 5, from 3 to 5; and may be about 5 motifs. Exemplary domain sequences are provided in, for example, SEQ ID NO:20 and 21. Examples include, without limitation, SEQ ID NO:1, LQ(LDASTVYAVGRGDSPASSA[(VPGIG)$_2$VPGKG(VPGIG)$_2$]$_3$)$_4$ and SEQ ID NO:2, LQ(LDASTVYAVGRDGSPASSA[(VPGIG)$_2$VPGKG(VPGIG)$_2$]$_3$)$_4$.

The ELP protein is chemically modified to comprise a pendant hydrazine group, and may comprise from about 3 to about 20 hydrazine groups, from about 5 to about 18, from about 10 to about 14 groups. Standard bioconjugation chemistry can be used to attach pendant hydrazines at sites of any of lysine, cysteine, or tyrosine amino acids.

TABLE 1

Amino-acid sequences for the bio-active domain and elastin-like region of HELP gels.

| ECM-derived Protein | Cell-adhesive domain | Elastin-Like Region |
|---|---|---|
| h-Fibronectin | (SEQ ID NO: 10) TVYAVTGRGDSPASSAA | (SEQ ID NO: 20) (VPGIG)$_2$(VPGKG)(VPGIG)$_2$ |

TABLE 1-continued

Amino-acid sequences for the bio-active domain and elastin-like region of HELP gels.

| ECM-derived Protein | Cell-adhesive domain | Elastin-Like Region |
|---|---|---|
| Laminin (ß1 chain) | (SEQ ID NO: 11) VSDPGYIGSRSDDSASASAA | (SEQ ID NO: 20) $(VPGIG)_2$(VPGKG)$(VPGIG)_2$ |
| Laminin (α1 chain) | (SEQ ID NO: 22) ARKQAASIKVAVSADRASA | (SEQ ID NO: 21) (VPGIG)(VPGKG)(VPGYG)(VPGIG)(VPGKG)(VPGIG) |
| Collagen I | (SEQ ID NO: 12) VGPAGGDGEAGAQGPP | (SEQ ID NO: 20) $(VPGIG)_2$(VPGKG)$(VPGIG)_2$ |
| h-Tenascin-C | (SEQ ID NO: 13) *SGSGGSGGPLAEIDGIELTYGGSGGSGS* | (SEQ ID NO: 20) $(VPGIG)_2$(VPGKG)$(VPGIG)_2$ |
| h-Tenascin-C | (SEQ ID NO: 14) *SGSGGSGGLDVFDNFVLKGGSGGSGS* | (SEQ ID NO: 21) (VPGIG)(VPGKG)(VPGYG)(VPGIG)(VPGKG)(VPGIG) |
| h-Tenascin-C | (SEQ ID NO: 15) *SGSGGSGGLDVFDNFVLGGSGGSGS* | (SEQ ID NO: 20) $(VPGIG)_2$(VPGKG)$(VPGIG)_2$ |
| N-cadherin | (SEQ ID NO: 16) SGSGGSGGHAVDIGGSGGSGS | (SEQ ID NO: 20) $(VPGIG)_2$(VPGKG)$(VPGIG)_2$ |
| N-cadherin | (SEQ ID NO: 17) SGSGGSGGHAVDINGHAVDIGGSGGSGS | (SEQ ID NO: 20) $(VPGIG)_2$(VPGKG)$(VPGIG)_2$ |
| Non-binding | (SEQ ID NO: 18) SGSGGSGGADHIVGGSGGSGS | (SEQ ID NO: 20) $(VPGIG)_2$(VPGKG)$(VPGIG)_2$ |
| Non-binding | (SEQ ID NO: 19) TVYAVTGRDGSPASSAA | (SEQ ID NO: 20) $(VPGIG)_2$(VPGKG)$(VPGIG)_2$ |

Hyaluronic acid is an anionic, non-sulfated glycosaminoglycan distributed widely throughout connective, epithelial, and neural tissues. Hyaluronic acid is a polymer of disaccharides, themselves composed of D-glucuronic acid and N-acetyl-D-glucosamine, linked via alternating β-(1→4) and β-(1→3) glycosidic bonds. Hyaluronic acid can be up to 25,000 disaccharide repeats in length. Polymers of hyaluronic acid can range in size from about 20 kDa to about 1.5 MDa; from about 20 Kda to.

The hyaluronic acid is chemically modified to comprise a pendant benzaldehyde or aldehyde side group. The HA is usually modified at from about 5% to about 30% of the available reactive groups, and may be from about 7% to about 20%, from about 10% to about 15%, and may be around 12% modified.

For an aldehyde functional group the carboxylic acid groups on HA are amidated with propargylamine, generating an HA-alkyne intermediate; then, copper click chemistry was used to react this alkyne with the azide moiety of a heterobifunctional small molecule containing an aldehyde functional group onto the HA, generating HA functionalized with aldehydes.

Benzaldehyde modification can be accomplished by first modifying HA to comprise alkyne groups at a desired concentration, e.g. from about 3% to about 30%. HA-alkynes are then modified with N-(2-azidoethyl)-4-formylbenzamide to generate HA-benzaldehyde.

The terms "active agent," "antagonist", "inhibitor", "drug" and "pharmacologically active agent" are used interchangeably herein to refer to a chemical material or compound which, when administered to an organism (human or animal) induces a desired pharmacologic and/or physiologic effect by local and/or systemic action.

As used herein, the terms "treatment," "treating," and the like, refer to obtaining a desired pharmacologic and/or physiologic effect, such as reduction of viral titer. The effect may be prophylactic in terms of completely or partially preventing a disease or symptom thereof and/or may be therapeutic in terms of a partial or complete cure for a disease and/or adverse effect attributable to the disease. "Treatment," as used herein, covers any treatment of a disease in a mammal, particularly in a human, and includes: (a) preventing the disease or a symptom of a disease from occurring in a subject which may be predisposed to the disease but has not yet been diagnosed as having it (e.g., including diseases that may be associated with or caused by a primary disease; (b) inhibiting the disease, i.e., arresting its development; and (c) relieving the disease, i.e., causing regression of the disease (e.g., reduction in viral titers).

The terms "individual," "host," "subject," and "patient" are used interchangeably herein, and refer to an animal, including, but not limited to, human and non-human primates, including simians and humans; rodents, including rats and mice; bovines; equines; ovines; felines; canines; avians, and the like. "Mammal" means a member or members of any mammalian species, and includes, by way of example, canines; felines; equines; bovines; ovines; rodentia, etc. and primates, e.g., non-human primates, and humans. Non-human animal models, e.g., mammals, e.g. non-human primates, murines, lagomorpha, etc. may be used for experimental investigations.

As used herein, the terms "determining," "measuring," "assessing," and "assaying" are used interchangeably and include both quantitative and qualitative determinations.

The terms "polypeptide" and "protein", used interchangeably herein, refer to a polymeric form of amino acids of any length, which can include coded and non-coded amino acids, chemically or biochemically modified or derivatized amino acids, and polypeptides having modified peptide backbones. The term includes fusion proteins, including, but not limited to, fusion proteins with a heterologous amino acid sequence, fusions with heterologous and native leader sequences, with or without N-terminal methionine residues; immunologically tagged proteins; fusion proteins with detectable fusion partners, e.g., fusion proteins including as a fusion partner a fluorescent protein, β-galactosidase, luciferase, etc.; and the like.

The terms “nucleic acid molecule” and “polynucleotide” are used interchangeably and refer to a polymeric form of nucleotides of any length, either deoxyribonucleotides or ribonucleotides, or analogs thereof. Polynucleotides may have any three-dimensional structure, and may perform any function, known or unknown. Non-limiting examples of polynucleotides include a gene, a gene fragment, exons, introns, messenger RNA (mRNA), transfer RNA, ribosomal RNA, ribozymes, cDNA, recombinant polynucleotides, branched polynucleotides, plasmids, vectors, isolated DNA of any sequence, control regions, isolated RNA of any sequence, nucleic acid probes, and primers. The nucleic acid molecule may be linear or circular.

A “therapeutically effective amount” or “efficacious amount” means the amount of a compound that, when administered to a mammal or other subject for treating a disease, condition, or disorder, is sufficient to effect such treatment for the disease, condition, or disorder. The “therapeutically effective amount” will vary depending on the compound, the disease and its severity and the age, weight, etc., of the subject to be treated.

The term “unit dosage form,” as used herein, refers to physically discrete units suitable as unitary dosages for human and animal subjects, each unit containing a predetermined quantity of a compound calculated in an amount sufficient to produce the desired effect in association with a pharmaceutically acceptable diluent, carrier or vehicle. The specifications for unit dosage forms depend on the particular compound employed and the effect to be achieved, and the pharmacodynamics associated with each compound in the host.

A “pharmaceutically acceptable excipient,” “pharmaceutically acceptable diluent,” “pharmaceutically acceptable carrier,” and “pharmaceutically acceptable adjuvant” means an excipient, diluent, carrier, and adjuvant that are useful in preparing a pharmaceutical composition that are generally safe, non-toxic and neither biologically nor otherwise undesirable, and include an excipient, diluent, carrier, and adjuvant that are acceptable for veterinary use as well as human pharmaceutical use. “A pharmaceutically acceptable excipient, diluent, carrier and adjuvant” as used in the specification and claims includes both one and more than one such excipient, diluent, carrier, and adjuvant.

As used herein, a “pharmaceutical composition” is meant to encompass a composition suitable for administration to a subject, such as a mammal, especially a human. In general a “pharmaceutical composition” is sterile, and preferably free of contaminants that are capable of eliciting an undesirable response within the subject (e.g., the compound(s) in the pharmaceutical composition is pharmaceutical grade). Pharmaceutical compositions can be designed for administration to subjects or patients in need thereof via a number of different routes of administration including oral, buccal, rectal, parenteral, intraperitoneal, intradermal, intracheal, intramuscular, subcutaneous, and the like.

The term “somatic cell” encompasses any cell in an organism that cannot give rise to all types of cells in an organism, i.e. it is not pluripotent. In other words, somatic cells are cells that have differentiated sufficiently that they will not naturally generate cells of all three germ layers of the body, i.e. ectoderm, mesoderm and endoderm.

The term “pluripotent” or “pluripotency” refers to cells with the ability to give rise to progeny that can undergo differentiation, under appropriate conditions, into cell types that collectively exhibit characteristics associated with cell lineages from the three germ layers (endoderm, mesoderm, and ectoderm). A “stem cell” is a cell characterized by the ability of self-renewal through mitotic cell division and the potential to differentiate into a tissue or an organ. Among mammalian stem cells, embryonic and somatic stem cells may be distinguished. Pluripotent stem cells, which include embryonic stem cells, embryonic germ cells and induced pluripotent cells, can contribute to tissues of a prenatal, postnatal or adult organism.

The terms “primary cells”, “primary cell lines”, and “primary cultures” are used interchangeably herein to refer to cells and cell cultures that have been derived from a subject and allowed to grow in vitro for a limited number of passages, i.e. splittings, of the culture. For example primary cultures are cultures that may have been passaged 0 times, 1 time, 2 times, 4 times, 5 times, 10 times, or 15 times, but not enough times go through the crisis stage. Typically, the primary cell lines of the present invention are maintained for fewer than 10 passages in vitro.

The subject cells may be from any mammal, including humans, primates, domestic and farm animals, and zoo, laboratory or pet animals, such as dogs, cats, cattle, horses, sheep, pigs, goats, rabbits, rats, mice etc. They may be established cell lines or they may be primary cells, where “primary cells”, “primary cell lines”, and “primary cultures” are used interchangeably herein to refer to cells and cells cultures that have been derived from a subject and allowed to grow in vitro for a limited number of passages.

The subject cells may be isolated from fresh or frozen cells, which may be from a neonate, a juvenile or an adult, and from tissues including skin, muscle, bone marrow, peripheral blood, umbilical cord blood, spleen, liver, pancreas, lung, intestine, stomach, adipose, and other differentiated tissues. The tissue may be obtained by biopsy or aphoresis from a live donor, or obtained from a dead or dying donor within about 48 hours of death, or freshly frozen tissue, tissue frozen within about 12 hours of death and maintained at below about −20° C., usually at about liquid nitrogen temperature (−190° C.) indefinitely. For isolation of cells from tissue, an appropriate solution may be used for dispersion or suspension. Such solution will generally be a balanced salt solution, e.g. normal saline, PBS, Hank’s balanced salt solution, etc., conveniently supplemented with fetal calf serum or other naturally occurring factors, in conjunction with an acceptable buffer at low concentration, generally from 5-25 mM. Convenient buffers include HEPES, phosphate buffers, lactate buffers, etc.

The term “cell culture” or “culture” means the maintenance of cells in an artificial, in vitro environment. It is to be understood, however, that the term “cell culture” is a generic term and may be used to encompass the cultivation not only of individual cells, but also of tissues or organs.

Culture conditions of interest provide an environment permissive for differentiation, in which stem or progenitor cells will proliferate, differentiate, or mature in vitro. Such conditions may also be referred to as differentiative conditions. Features of the environment include the medium in which the cells are cultured, any growth factors or differentiation-inducing factors that may be present, and a supporting structure of a hydrogel as disclosed herein. Differentiation may be initiated by formation of organoids, or similar structures.

A "long term culture" used herein refers to a culture in which cells grow, differentiate and are viable for at least about 10 days, or more than 30 days, or more than 60 days, or more than 100 days or more than 150 days.

Stem cell: The term stem cell is used herein to refer to a mammalian cell that has the ability both to self-renew, and to generate differentiated progeny (see Morrison et al. (1997) Cell 88:287-298). Generally, stem cells also have one or more of the following properties: an ability to undergo asynchronous, or asymmetric replication, that is where the two daughter cells after division can have different phenotypes; extensive self-renewal capacity; capacity for existence in a mitotically quiescent form; and clonal regeneration of all the tissue in which they exist, for example the ability of hematopoietic stem cells to reconstitute all hematopoietic lineages. "Progenitor cells" differ from stem cells in that they typically do not have the extensive self-renewal capacity, and often can only regenerate a subset of the lineages in the tissue from which they derive, for example only lymphoid, or erythroid lineages in a hematopoietic setting.

Stem cells may be characterized by both the presence of markers associated with specific epitopes identified by antibodies and the absence of certain markers as identified by the lack of binding of specific antibodies. Stem cells may also be identified by functional assays both in vitro and in vivo, particularly assays relating to the ability of stem cells to give rise to multiple differentiated progeny.

"Lineage-committed stem cells" is used herein to refer to multipotent stem cells that give rise to cells of specific lineage, e.g. mesodermal stem cells (see, e.g. Reyes et al. (2001) Blood 98:2615-2625; Eisenberg & Bader (1996) Circ Res. 78(2):205-16; etc.)

"Tissue-specific stem cells" is used herein to refer to multipotent stem cells that reside in a particular tissue and are capable of clonal regeneration of cells of the tissue in which they reside, for example the ability of hematopoietic stem cells to reconstitute all hematopoietic lineages, or the ability of neuronal stem cells to reconstitute all neuronal/glial lineages. "Progenitor cells" differ from tissue-specific stem cells in that they typically do not have the extensive self-renewal capacity, and often can only regenerate a subset of the lineages in the tissue from which they derive, for example only lymphoid or erythroid lineages in a hematopoietic setting, or only neurons or glia in the nervous system.

Stem cells and cultures thereof: Pluripotent stem cells are cells derived from any kind of tissue (usually embryonic tissue such as fetal or pre-fetal tissue), which stem cells have the characteristic of being capable under appropriate conditions of producing progeny of different cell types that are derivatives of all of the 3 germinal layers (endoderm, mesoderm, and ectoderm). These cell types may be provided in the form of an established cell line, or they may be obtained directly from primary embryonic tissue and used immediately for differentiation. Included are cells listed in the NIH Human Embryonic Stem Cell Registry, e.g. hESBGN-01, hESBGN-02, hESBGN-03, hESBGN-04 (BresaGen, Inc.); HES-1, HES-2, HES-3, HES-4, HES-5, HES-6 (ES Cell International); Miz-hES1 (MizMedi Hospital-Seoul National University); HSF-1, HSF-6 (University of California at San Francisco); and H1, H7, H9, H13, H14 (Wisconsin Alumni Research Foundation (WiCell Research Institute)).

Stem cells of interest also include embryonic cells of various types, exemplified by human embryonic stem (hES) cells, described by Thomson et al. (1998) Science 282:1145; embryonic stem cells from other primates, such as Rhesus stem cells (Thomson et al. (1995) Proc. Natl. Acad. Sci USA 92:7844); marmoset stem cells (Thomson et al. (1996) Biol. Reprod. 55:254); and human embryonic germ (hEG) cells (Shamblott et al., Proc. Natl. Acad. Sci. USA 95:13726, 1998). Also of interest are lineage committed stem cells, such as mesodermal stem cells and other early cardiogenic cells (see Reyes et al. (2001) Blood 98:2615-2625; Eisenberg & Bader (1996) Circ Res. 78(2):205-16; etc.) The stem cells may be obtained from any mammalian species, e.g. human, equine, bovine, porcine, canine, feline, rodent, e.g. mice, rats, hamster, primate, etc.

ES cells are considered to be undifferentiated when they have not committed to a specific differentiation lineage. Such cells display morphological characteristics that distinguish them from differentiated cells of embryo or adult origin. Undifferentiated ES cells are easily recognized by those skilled in the art, and typically appear in the two dimensions of a microscopic view in colonies of cells with high nuclear/cytoplasmic ratios and prominent nucleoli. Undifferentiated ES cells express genes that may be used as markers to detect the presence of undifferentiated cells, and whose polypeptide products may be used as markers for negative selection. For example, see US 2003/0224411 A1; Bhattacharya (2004) Blood 103(8):2956-64; and Thomson (1998), supra., each herein incorporated by reference. Human ES cell lines express cell surface markers that characterize undifferentiated nonhuman primate ES and human EC cells, including stage-specific embryonic antigen (SSEA)-3, SSEA-4, TRA-I-60, TRA-1-81, and alkaline phosphatase. The globo-series glycolipid GL7, which carries the SSEA-4 epitope, is formed by the addition of sialic acid to the globo-series glycolipid Gb5, which carries the SSEA-3 epitope. Thus, GL7 reacts with antibodies to both SSEA-3 and SSEA-4. The undifferentiated human ES cell lines did not stain for SSEA-1, but differentiated cells stained strongly for SSEA-I. Methods for proliferating hES cells in the undifferentiated form are described in WO 99/20741, WO 01/51616, and WO 03/020920.

As used herein, "reprogramming factors" refers to one or more, i.e. a cocktail, of biologically active factors that act on a cell to alter transcription, thereby reprogramming a cell to multipotency or to pluripotency. Reprogramming factors may be provided to the cells, e.g. cells from an individual with a family history or genetic make-up of interest for heart disease such as fibroblasts, adipocytes, etc.; individually or as a single composition, that is, as a premixed composition, of reprogramming factors. The factors may be provided at the same molar ratio or at different molar ratios. The factors may be provided once or multiple times in the course of culturing the cells of the subject invention. In some embodiments the reprogramming factor is a transcription factor, including without limitation, Oct3/4; Sox2; Klf4; c-Myc; Nanog; and Lin-28.

Somatic cells are contacted with reprogramming factors, as defined above, in a combination and quantity sufficient to reprogram the cell to pluripotency. Reprogramming factors may be provided to the somatic cells individually or as a single composition, that is, as a premixed composition, of reprogramming factors. In some embodiments the reprogramming factors are provided as a plurality of coding sequences on a vector.

Genes may be introduced into the somatic cells or the iPS cells derived therefrom for a variety of purposes, e.g. to replace genes having a loss of function mutation, provide marker genes, etc. Alternatively, vectors are introduced that express antisense mRNA or ribozymes, thereby blocking expression of an undesired gene. Other methods of gene therapy are the introduction of drug resistance genes to enable normal progenitor cells to have an advantage and be subject to selective pressure, for example the multiple drug resistance gene (MDR), or anti-apoptosis genes, such as bcl-2. Various techniques known in the art may be used to introduce nucleic acids into the target cells, e.g. electroporation, calcium precipitated DNA, fusion, transfection, lipofection, infection and the like, as discussed above. The particular manner in which the DNA is introduced is not critical to the practice of the invention.

The term "intestinal cells" used herein denotes cells that make up the mammalian intestinal epithelium. The mammalian intestinal epithelium of the gastrointestinal tract has a well-defined organizational structure. The epithelium can be divided into two regions, a functional region that houses differentiated cells (villi) and a proliferative region (crypts of Lieberkuhn) that represents the epithelium stem cell niche. Multipotent epithelium stem cells reside in the crypts and give rise to four principal epithelial lineages: absorptive enterocytes, mucin secreting goblet cells, peptide hormone secreting enteroendocrine cells, and Paneth cells.

The phrase "mammalian intestinal cells" means cells originating from mammalian intestine. Typically, in the methods of the invention pieces of intestine can be obtained surgically and minced to a size less than about 1 $mm^3$, and may be less than about 0.5 $mm^3$, or less than about 0.1 $mm^3$, or alternatively to be dissociated into single cells. Mammalian used herein includes human, equine, bovine, porcine, canine, feline, rodent, e.g. mice, rats, hamster, primate, etc. Intestinal tissue can be obtained from humans by biopsy during endoscopy. "Mammalian intestinal cells" and "intestinal cells" and "intestinal epithelial cells" have been used interchangeably. The source of the intestinal tissue can be fetus, neonate, juvenile, or adult.

"Intestine" refers to the mammalian small intestine and mammalian large intestine. For the methods described herein the intestinal tissue is obtained either from the small or from the large intestine.

The term "explant" means cells originating from mammalian intestinal tissue, and grown from in vitro, for example according to the methods of the invention.

"Intestinal stem cells" is used interchangeably with "epithelial stem cells" to refer to stem cells that have the potential to proliferate and differentiate into intestinal epithelial cells. Multipotent epithelial stem cells give rise to various epithelial lineages, and may give rise to all intestinal epithelial lineages, which include: absorptive enterocytes, mucin secreting-goblet cells, peptide hormone secreting enteroendocrine cells, and Paneth cells.

The term "multi-lineage differentiation markers" means differentiation markers characteristic of different cell-types. These differentiation markers can be detected by using an affinity reagent, e.g. antibody specific to the marker, by using chemicals that specifically stain a cell type, etc as known in the art. Non-limiting examples of terminal differentiation markers include chromogranin A, NeuroD-enteroendocrine cells; mucin-goblet cells; villin, CD10-enterocytes, Lysozyme, Ang4-Paneth cells. Common progenitors for enteroendocrine, goblet and Paneth cells are detected by using an antibody against Math1. P-PTEN, SFRPS and Musashil are specifically expressed in intestinal stem cells and intestinal progenitor cells. Intestinal alkaline phosphatase (IAP) marks enterocytes.

The term "candidate agents" means oligonucleotides, polynucleotides, siRNA, shRNA genes, gene products, small molecules and pharmacological compounds that is introduced in the intestinal cell culture described herein to assay for their effect on the explants.

The term "contacting" refers to the placing either candidate cells or candidate agents in the explant culture of mammalian intestinal cells. Contacting also encompasses co-culture of candidate cells with intestinal explants for at least 1 hour, or more than 2 hrs or more than 4 hrs in culture medium prior to placing them in a semi-permeable substrate. Alternatively, contacting refers to placing via trans-luminal injection, candidate cells into the lumen of explants growing as cysts.

"Screening" refers to the process of either co-culturing candidate cells with or adding candidate agents to a culture described herein. The effect of the candidate cells or candidate agents on a culture is assessed by an increase in growth of the explants over basal levels and by presence of multilineage differentiation markers, for example indicative of intestinal stem cells. The effect of candidate cells or candidate agents on the intestinal explant can be further evaluated by assaying the intestinal explant for long-term reconstitutive activity by serial in vitro passage, as well as by in vivo transplantation by subcutaneous implant assay and renal capsule assay.

By "container" is meant a glass, plastic, or metal vessel that can provide an aseptic environment for culturing cells.

The term "explant" is used herein to mean a piece of tissue and the cells thereof originating from mammalian tissue that is cultured in vitro, for example according to the methods of the invention. The mammalian tissue from which the explant is derived may obtained from an individual, i.e. a primary explant, or it may be obtained in vitro, e.g. by differentiation of induced pluripotent stem cells.

The term "organoid" is used herein to mean a 3-dimensional growth of mammalian cells in culture that retains characteristics of the tissue in vivo, e.g. prolonged tissue expansion with proliferation, multilineage differentiation, recapitulation of cellular and tissue ultrastructure, etc. A primary organoid is an organoid that is cultured from an explant, i.e. a cultured explant. A secondary organoid is an organoid that is cultured from a subset of cells of a primary organoid, i.e. the primary organoid is fragmented, e.g. by mechanical or chemical means, and the fragments are replated and cultured. A tertiary organoid is an organoid that is cultured from a secondary organoid, etc.

"Ultrastructure" refers to the three-dimensional structure of a cell or tissue observed in vivo. For example, the ultrastructure of a cell may be its polarity or its morphology in vivo, while the ultrastructure of a tissue would be the arrangement of different cell types relative to one another within a tissue.

"Screening" refers to the process of either co-culturing candidate cells with or adding candidate agents to the culture described herein and assessing the effect of the candidate cells or candidate agents on the culture. The effect may be assessed by assessing any convenient parameter, e.g. the growth rate of the explant, the presence of multilineage differentiation markers indicative of stem cells, etc. The effect of candidate cells or candidate agents on the explant can be further evaluated by assaying the explant for long-term reconstitutive activity by serial in vitro passage, as well as by in vivo transplantation.

Culture Methods

Culture systems and methods are provided for culture of various mammalian tissues. In some embodiments, tissue, i.e. primary tissue, is obtained from a mammalian organ. The tissue may be from any mammalian species, e.g. human, equine, bovine, porcine, canine, feline, rodent, e.g. mice, rats, hamster, primate, etc. The mammal may be of any age, e.g. a fetus, neonate, juvenile, adult. The following are some non-limiting examples of tissues that may be obtained for the purposes of preparing organoids. Cells or tissue may be obtained by any convenient method, e.g. by biopsy, e.g. during endoscopy, during surgery, by needle, etc., or from cell lines, in vitro differentiation etc. If tissue, it is immersed in ice-cold buffered solution, e.g. PBS, Ham's F12, MEM, culture medium, etc. Pieces of tissue are minced to a size less than about 1 $mm^3$, and may be dissociated to single cells. The minced tissue is mixed with a hydrogel of the disclosure. Subsequently, the cell-containing hydrogel is placed into suitable medium.

In some embodiments, tissue is grown in vitro from pluripotent stem cells, e.g. embryonic stem cells (ESCs), embryonic germ cells (EGCs), induced pluripotent stem cells (iPSCs). Any convenient method may be followed for the induction of the desired tissue from pluripotent stem cells. The engineered tissue can transferred to hydrogel substrate.

The continued growth of explants may be confirmed by any convenient method, e.g. phase contrast microscopy, stereomicroscopy, histology, immunohistochemistry, electron microscopy, etc. In some instances, cellular ultrastructure and multi-lineage differentiation may be assessed. Ultrastructure of the intestinal explants in culture can be determined by performing Hematoxylin-eosin staining, PCNA staining, electron microscopy, and the like using methods known in the art. Multi-lineage differentiation can be determined by performing labeling with antibodies to terminal differentiation markers, e.g. as described in greater detail below. Antibodies to detect differentiation markers are commercially available from a number of sources.

In some embodiments, the cells in the cultured explants may be experimentally modified. For example, the explant cells may be modified by exposure to viral or bacterial pathogens, e.g. to develop a reagent for experiments to assess the anti-viral or anti-bacterial effects of therapeutic agents. The explant cells may be modified by altering patterns of gene expression, e.g. by providing reprogramming factors to induce pluripotency or otherwise alter differentiation potential, or to determine the effect of a gain or loss of gene activity on the ability of cells to form an explant culture or on the ability of cells to undergo tumor transformation. The explant cells may be modified such that they are transformed into proto-oncogenic or oncogenic cells, e.g. by providing cancer drivers—oncogenic factors or inhibitors of tumor suppressor genes, e.g. nucleic acids for the overexpression of Kras.sup.G12D; nucleic acids that suppress expression of APC, p53, or Smad4, etc., for example, to assess the effects of therapeutic agents on tumors.

Experimental modifications may be made by any method known in the art, for example, as described below with regard to methods for providing candidate agents that are nucleic acids, polypeptides, small molecules, viruses, etc. to explants and the cells thereof for screening purposes.

Organoids prepared by the subject methods find use in many applications. For example, cancer, ischemia, congenital syndromes, trauma, and inflammation can produce functional loss or mandate physical resection of large sections of patient tissue extensive enough to compromise organ physiology. The ability to grow explants of mammalian tissue in vitro to be placed back into such patients or to be used as a source of tissue-specific stem cells for transplantation into such patients is a valuable treatment option. Such cells can augment the ex vivo expansion of tissue, providing an autologous source of engineered tissue and/or tissue stem cells. As another example, organoids prepared by the subject methods may be used to predict the responsiveness of an individual, e.g. an individual with cancer, with an infection, etc., to a therapy. As another example, organoids prepared by the subject methods may be used in basic research, e.g. to better understand the basis of disease, and in drug discovery, e.g. as reagents in screens such as those described further below. Organoids are also useful for assessing the pharmacokinetics and pharmacodynamics of an agent, e.g. the ability of a mammalian tissue to absorb an active agent, the cytotoxicity of agents on primary mammalian tissue or on oncogenic mammalian tissue, etc.

EXPERIMENTAL

Engineered Matrices Permit the Formation, Growth, Passaging, and Differentiation of Human Patient-Derived Intestinal Organoids Human intestinal organoids derived from primary tissue of patient biopsies have the potential to revolutionize personalized medicine and preclinical models of human gastrointestinal disease. To date, most intestinal organoids are grown in a decellularized matrix derived from Engelbreth-Holm-Swarm (EHS) mouse sarcoma, materials that have limited tunability and reproducibility. To overcome this limitation, we report a designer matrix, termed Hyaluronan Elastin-Like Protein (HELP), that enables the formation, differentiation, and passaging of adult primary tissue-derived, epithelial-only intestinal organoids. These materials enable the encapsulation of dissociated patient-derived cells, which then undergo proliferation and de novo formation of enteroids, spherical structures with polarized internal lumens. After 12 rounds of passaging, dissociation, and reformation of human enteroids, growth in HELP materials was found to be statistically similar to that in EHS matrices. HELP materials further supported the differentiation of human enteroids into more specialized cell types: Paneth cells, goblet cells, and enteroendocrine cells. Three critical variables of HELP—matrix stiffness, matrix stress relaxation rate, and matrix integrin-ligand concentration—can each be independently and quantitatively specified, enabling fundamental studies of organoid-matrix interactions and potential patient-specific optimization. We find that organoid formation in HELP materials is most robust in gels with stiffer moduli (G'~1 kPa), slower stress relaxation rate ($t_{1/2}$~18 hrs), and higher integrin ligand concentration (0.5-1 mM RGD peptide). Our material provides a 3D in vitro model for further understanding organoid development and disease in humans and a reproducible, biodegradable, minimal matrix with no animal-derived products or synthetic polyethylene glycol for potential clinical translation.

Synthetic matrices have been designed that support the formation of murine and human induced pluripotent stem cell (iPSC)-derived organoids without requiring EHS matrix or other cell types. In contrast, human patient-derived intestinal organoids in synthetic matrices have often required either a spheroid formation step in EHS matrix or co-culture with mesenchymal cells. Recent work to develop engineered matrices for patient-derived intestinal organoids have relied on polyethylene glycol (PEG) as a synthetic matrix backbone, although PEG is known to interact with the immune system and induce antibody formation. To create a PEG-free system, we report a designer matrix, Hyaluronan Elastin- Like Protein (HELP), that enables the formation, differentiation, and passaging of adult primary tissue-derived, epithelial-only intestinal organoids. Three critical variables of HELP (matrix stiffness, matrix stress relaxation rate, and matrix integrin-ligand concentration) can each be independently and quantitatively specified, enabling fundamental studies of organoid-matrix interactions and potential patient-specific optimization. Our material provides a 3D in vitro model for further understanding intestinal development and enteric disease in humans and a reproducible, biodegradable, minimal matrix with no animal-derived products or synthetic PEG for potential clinical translation.

We hypothesized that a minimal matrix inspired by biopolymers found in the native intestine would support the formation of organoids derived from primary human tissue (FIG. 1*a*). Our group previously reported a protein-engineered matrix that supported the formation and growth of primary murine intestinal organoids using amino acid sequences derived from human elastin and fibronectin. Elastin is one of the major components of the intestinal extracellular matrix (ECM), and fibronectin is expressed within the intestinal stem cell (ISC) crypt. Our recombinant elastin-like protein (ELP, MW 37.7 kDa) intersperses elastin-like sequences with an integrin-binding, extended RGD sequence borrowed from fibronectin (FIG. 1*b*, FIG. S1*a*). In vivo, ISC maintenance and proliferation is mediated in part by the CD44 receptor, with CD44 activation associated with intestinal growth. The CD44 receptor can interact with hyaluronan (HA, MW 100 kDa), a glycosaminoglycan important for normal intestinal growth, leading us to hypothesize that an engineered matrix that included HA could support patient-derived enteroid cultures. To create reproducible hydrogel materials from these two biopolymer components, we chemically modified ELP with hydrazine groups, as previously reported, and developed a scheme to chemically modify HA with benzaldehyde (FIG. 5*b-e*). Simply mixing the two modified biopolymers together induced the formation of hydrazone bonds resulting in a hydrogel network we term HELP.

Figure 6:
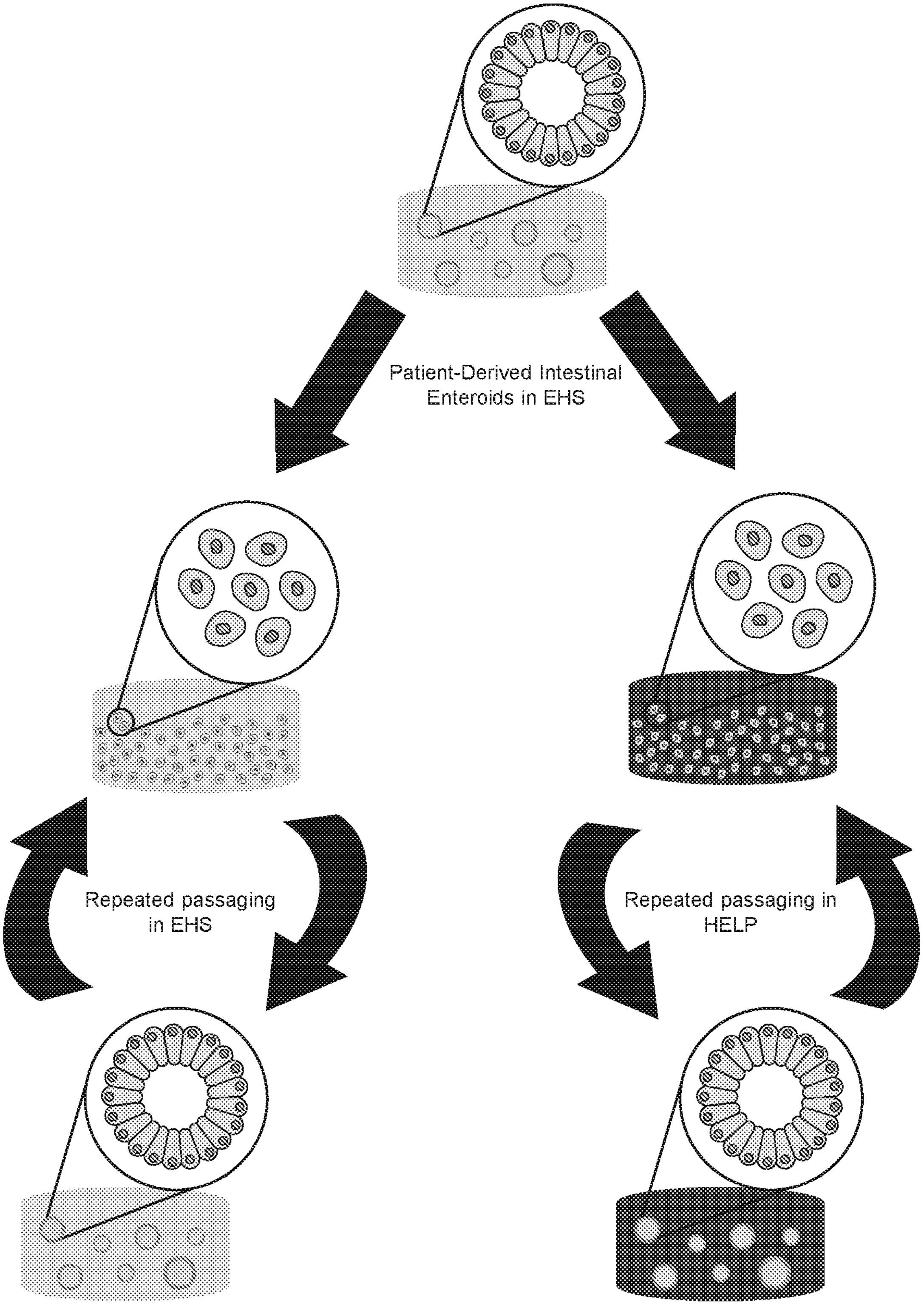
FIG. 6: Intestinal organoids can be passaged within EHS or HELP matrices. Single patient-derived intestinal cells can be seeded in either EHS or HELP matrices and repeatedly passaged from single cells.
Figure 7:
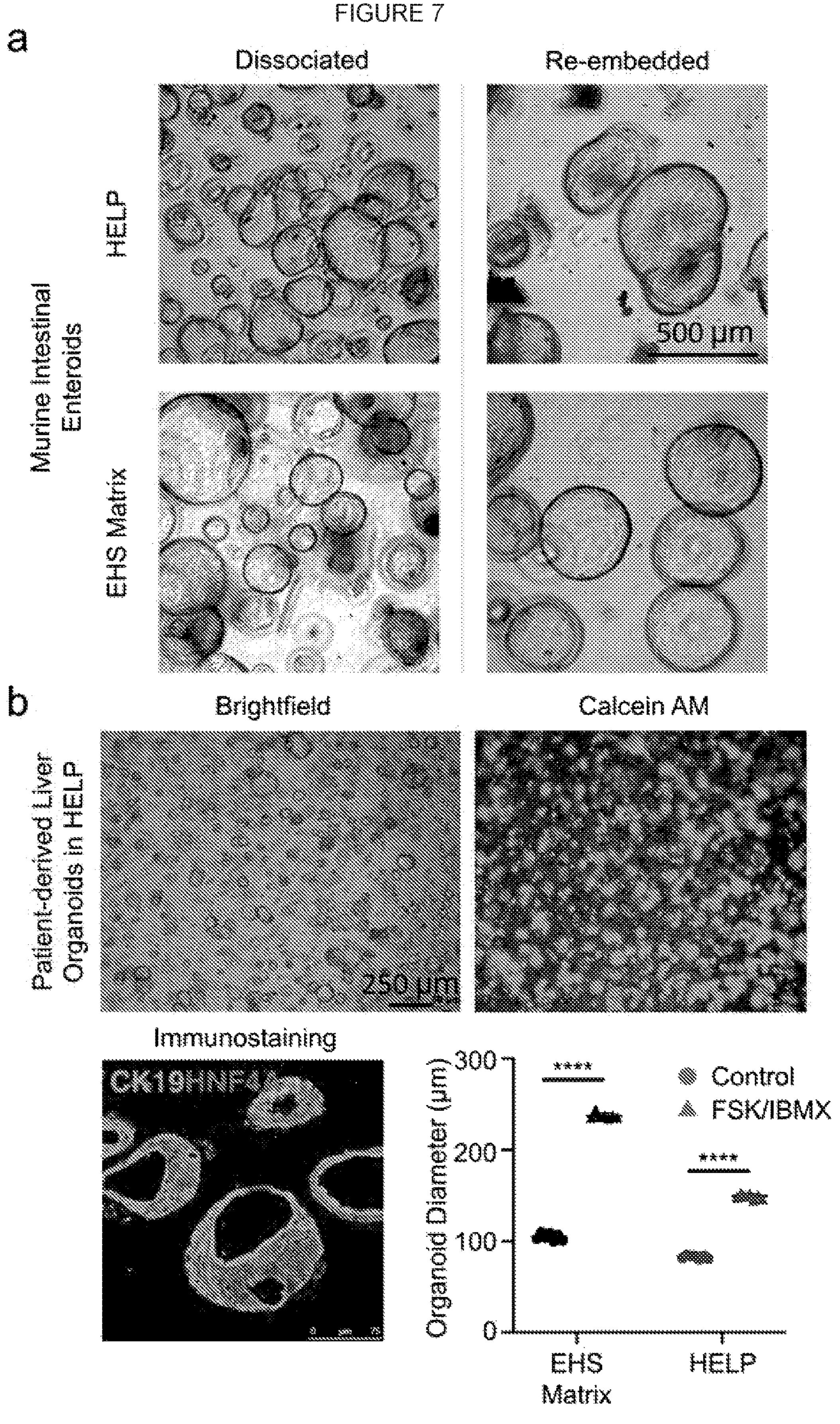
FIG. 7: Human intestinal organoids robustly form in HELP in more than one patient-derived cell line. a) Brightfield and confocal fluorescence micrographs of spheroids in EHS, HELP, and ELP only matrices, when dissociated (left) and re-embedded (right). b) Spheroid formation efficiency of spheroids grown from single cells in the material formulations shown in a). 1-way ANOVA with Tukey's multiple comparisons testing, ****=$p<0.0001$, n.d.=none detected. c) Representative brightfield images of spheroids grown at Passage 1 and Passage 4 in HELP, with dissociation into single cells at the time of each passage.
Figure 8:
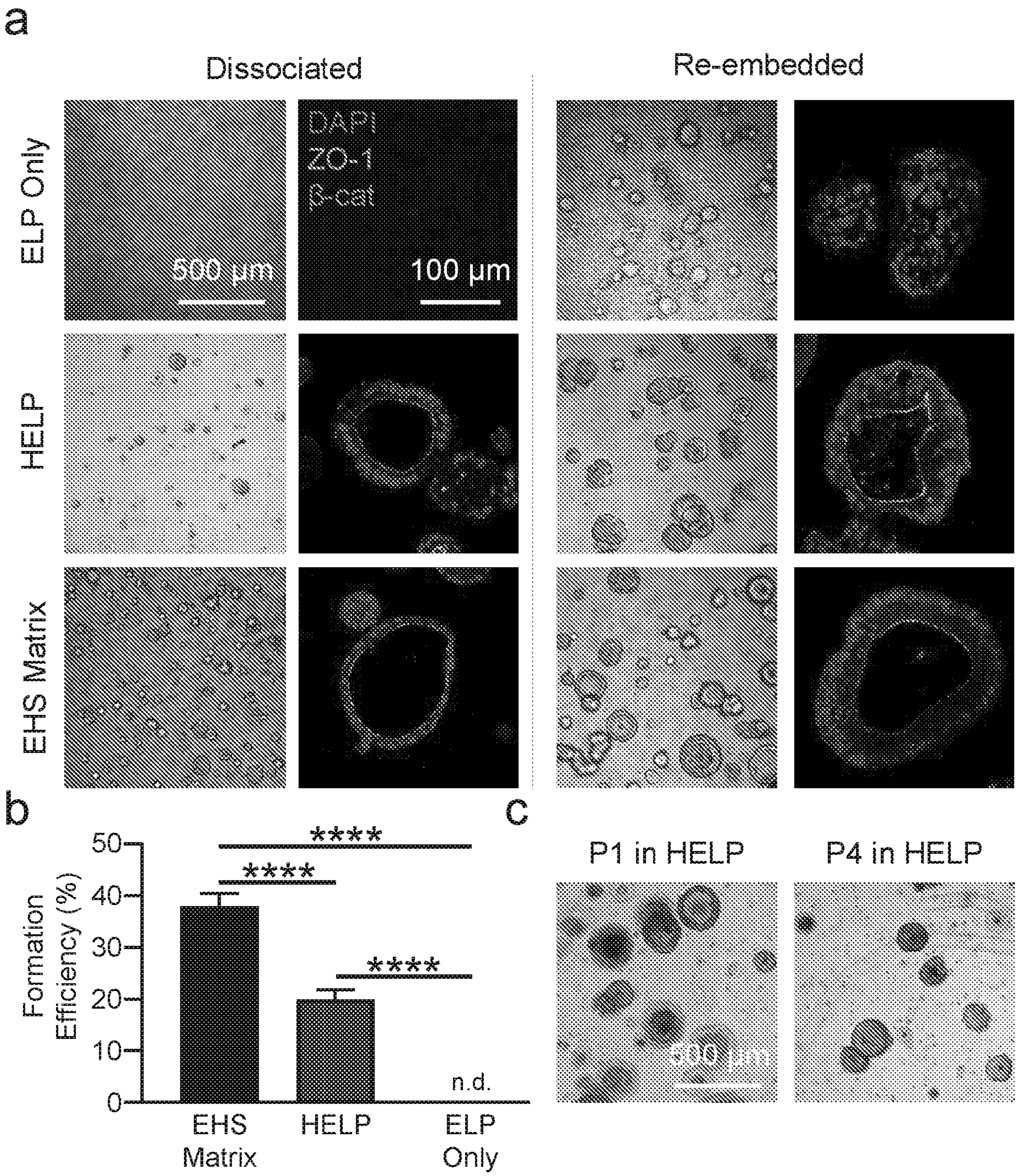
FIG. 8: HELP supports organoid formation and growth from murine intestinal cells and human iPSC-derived hepatic organoids. a) Brightfield micrographs of murine small intestinal spheroids grown in HELP and EHS matrices, when dissociated (left) and re-embedded (right). b) Micrographs of human hepatic organoids in HELP, by brightfield (top left), Calcein AM fluorescence (top right) and immunostaining for cytokeratin-19 (CK19) and hepatocyte nuclear factor 4 alpha (HNF4A) (bottom left). Quantification of human hepatic organoid size change in functional assay to show response to forskolin/IBMX (3-isobutyl-1-methylxanthine) treatment (bottom right). ****=$p<0.0001$.

Throughout this work, we classify cells in the following way: we refer to undifferentiated spheroids of intestinal epithelial cells as patient-derived intestinal enteroids (or more simply, enteroids); upon differentiation, we term these intestinal cell structures patient-derived intestinal organoids. In some work, what we term the enteroid state is referred to as an ISC colony or spheroid, in particular in murine systems where fluorescent reporter lines for $Lgr5^+$ ISC populations are utilized. Here, human enteroids were dissociated into single cells and embedded within HELP during covalent crosslinking of the hydrogel. Within three days, de novo spheroid formation was observed (FIG. 1*c,d*). Some previous reports of human enteroids in synthetic materials required an initial step of enteroid formation in EHS matrix before encapsulation in synthetic biomaterials, a process we term “re-embedding” (FIG. 1*c*). Therefore, we compared the ability of different materials to support these two distinct culture methods: 1) encapsulation of dissociated single cells and 2) re-embedding of pre-formed enteroids (FIG. 1*d*). As expected and consistent with previous reports, re-embedded enteroids were able to grow and remain viable for at least 6 days within ELP-only matrices that contain the fibronectin-derived, integrin-binding RGD ligand, although we note that enteroid polarization, as observed by ZO-1 and β-catenin staining, was not maintained (FIG. 1*d*, top). In stark contrast, dissociated human intestinal cells within the ELP-only matrix (i.e. without HA) were unable to form enteroids, suggesting that the RGD ligand alone is insufficient to support de novo organoid formation in this material. Interestingly, adding HA to the engineered matrix enabled single intestinal cells to robustly form enteroids in HELP, as well as survive at least 6 days when cultured as re-embedded enteroids (FIG. 6). Importantly, enteroids formed in HELP exhibited proper intestinal epithelial polarity, similar to EHS matrix, as indicated by the localization of the tight junction protein zonula occludens-1 (ZO-1) to the apical lumen and by basolateral localization of the adherens junction protein β-catenin (FIG. 1*d*). Similar results were observed for a second, distinct patient line within HELP matrices (FIG. 7). To demonstrate the potential broad applicability of HELP matrices to support organoid growth, primary murine intestinal enteroids and human induced pluripotent stem cell (iPSC)-derived hepatic organoids were also viable in HELP matrices (FIG. 8).

In addition to robust organoid formation from single cells, human enteroids within HELP can be repeatedly passaged and continue to form new enteroids after each passage (FIG. 1*e*, 6, 7*b,c*). HELP matrices are enzymatically degraded using elastase and hyaluronidase, followed by enteroid dissociation into single cells with trypsin (see Methods). Encapsulation of these single cells into fresh HELP matrix resulted in successful new enteroid formation for up to 12 passages without visible change in morphology (FIG. 1*e,f*). Enteroids that had been passaged repeatedly in HELP matrices matched the growth rate of enteroids in EHS matrix, as observed by brightfield microscopy over 12 days of culture (FIG. 1*f*). Furthermore, these repeatedly passaged enteroids had statistically similar formation rates in HELP and EHS matrices (FIG. 1*g*).

To assess whether HELP could support differentiation into patient-derived intestinal organoids, single cells embedded in HELP were first allowed to form enteroids for 10 days in growth medium, containing Wnt3A, Epidermal Growth Factor, Noggin, and R-spondin1 (FIG. 2*a*). While in growth medium, cells undergo initial enteroid formation (FIG. 2*b*, left). As the enteroids develop, the cells became columnar in morphology and adopt native intestinal apicobasal polarity, demonstrated by the thick apical actin border within the organoid (FIG. 2*b*, center) and localization of known polarization markers (FIG. 1*d*). On day 10, Wnt and R-spondin1 were removed to promote enteroid differentiation into organoids over 5 days.

This process resulted in the formation of undulating lumens containing differentiated intestinal cell types (FIG. 2*b*). Immunocytochemistry confirmed lysozyme-positive Paneth cells in organoids grown both in HELP and in EHS matrices (FIG. 2*c*). Higher expression of mucin-2 (Muc2)-positive goblet cells was observed in organoids grown in HELP compared to those grown in EHS matrix. Cells positive for chromogranin-A (ChgA), a marker of differentiated enteroendocrine cells, were identified in the HELP matrix, but could not be found in the EHS matrix. To assess the transcriptional expression of these differentiation markers, reverse transcription quantitative polymerase chain reaction (RT-qPCR) was performed on organoids differentiated in HELP or EHS matrices compared to enteroids that were maintained in growth medium in their respective matrices for 15 days (FIG. 2*d*). LYZ1 (lysozyme) and enterocyte marker VIL1 (villin-1) expression levels were relatively unchanged compared to the undifferentiated controls in both HELP and EHS matrix. A high upregulation of MUC2 (mucin-2) and CHGA (chromogranin-A) gene expression was observed in both HELP and EHS matrix.

Figure 9:
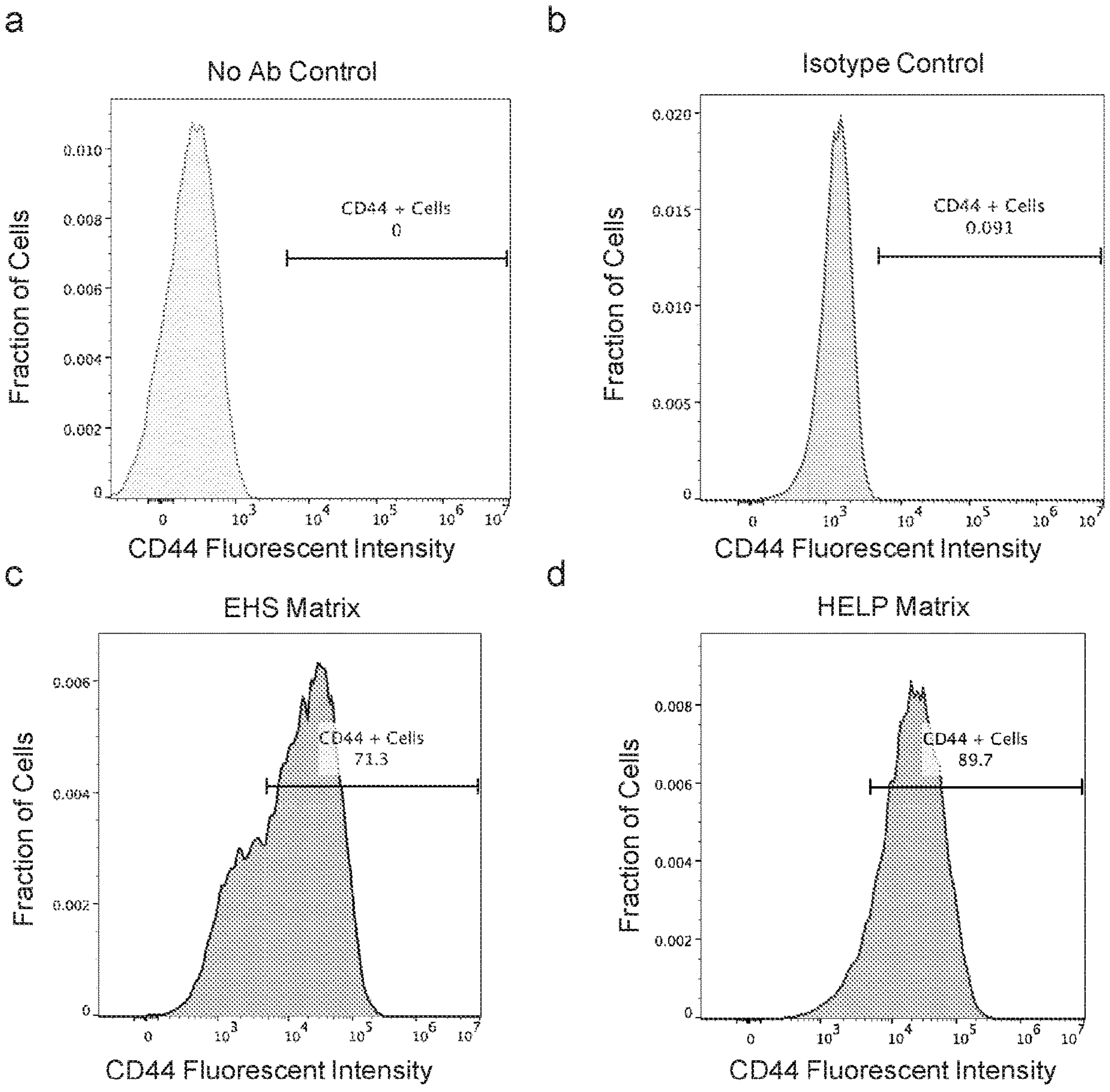
FIG. 9: Flow cytometric analysis for $CD44^+$ cells in enteroids grown in HELP and EHS matrices. a) Percent $CD44^+$-gated cells without the addition of any antibody. b) Percent $CD44^+$-gated cells stained with an isotype antibody control. c) Percent $CD44^+$-gated cells formed in EHS matrix. d) Percent $CD44^+$-gated cells grown in HELP.

Because enteroids were successfully formed in HELP but not ELP-only matrices (FIG. 1), we next sought to further explore the permissive role of HA in these matrices. To confirm that patient-derived intestinal cells express CD44, which is enriched in proliferative intestinal crypts and is also an HA receptor, we performed immunocytochemistry on enteroids formed from single cells in HELP and EHS matrices. Interestingly, a higher intensity of CD44 staining on the periphery of enteroids grown in HELP compared to EHS matrix was observed (FIG. 3*a*). Flow cytometry further confirmed this finding, as higher surface expression of CD44 was observed on single dissociated cells from enteroids grown in HELP compared to those grown in EHS matrices (FIG. 3*b*, FIG. 9). Flow cytometric analysis revealed that nearly 90 percent of cells from enteroids grown in HELP were CD44 positive, compared to 70 percent CD44-positive cells from enteroids grown in EHS matrix. These results suggest that HA signaling in HELP may play an important role in promoting enteroid formation. To further test whether HA signaling was a key feature of our material that assisted in enteroid formation, we modified a synthetic PEG polymer with the same benzaldehyde moiety that we used to modify our HA component. Using this material, we generated an ELP-PEG hydrogel matrix that was stiffness-matched to the HELP matrix (FIG. 10), with an equivalent concentration of RGD peptide (1 mM). Brightfield and confocal fluorescence microscopy revealed that enteroids were unable to form in ELP-PEG gels of equivalent mechanical properties to HELP, suggesting that HA biochemical signaling is a required component of the HELP matrix (FIG. 3*c,d*).

Figure 10:
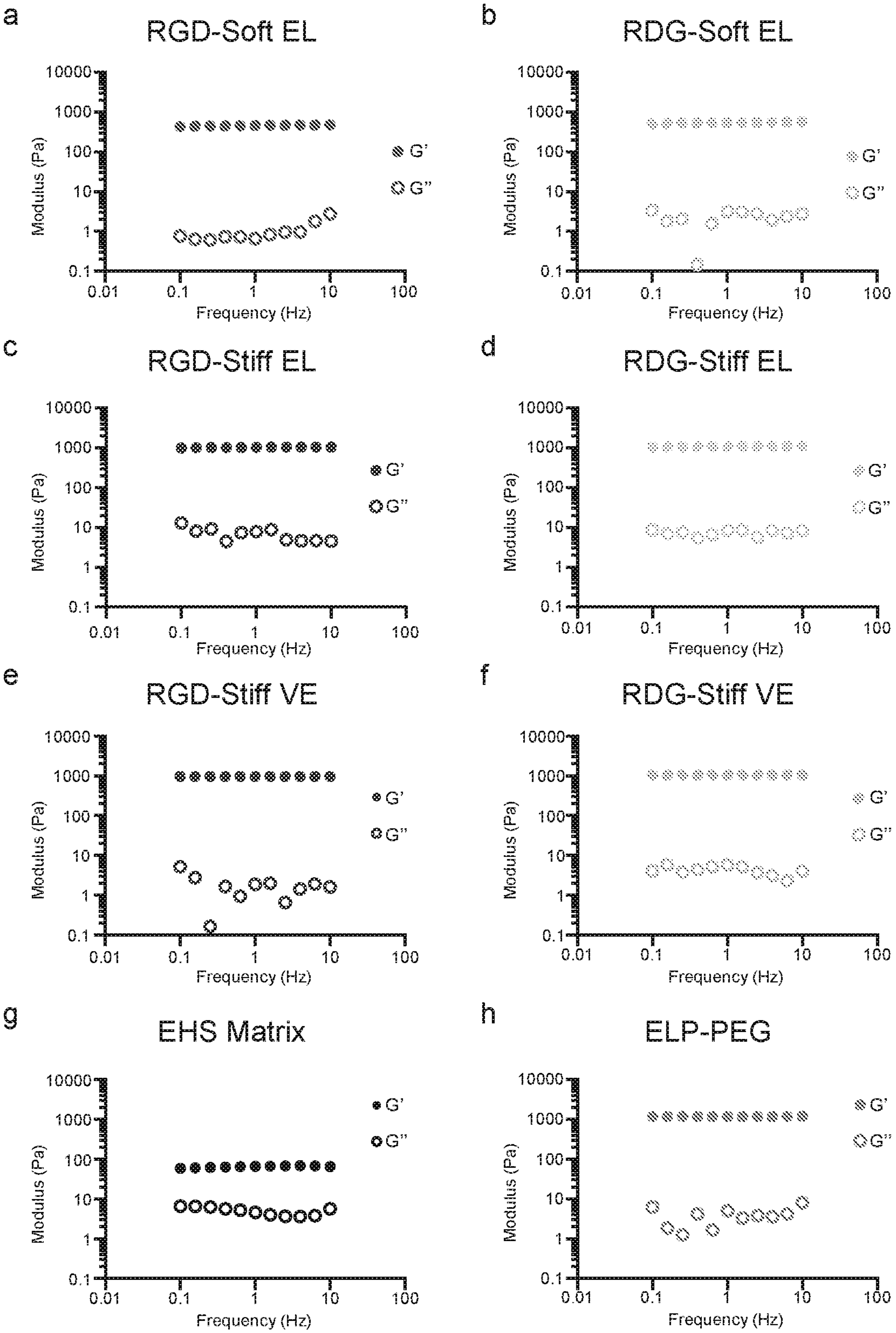
FIG. 10: Material rheology. a-g) Oscillatory shear rheology was performed to characterize the viscoelastic properties of all hydrogel formulations reported in this work. These frequency sweeps were performed between 0.1-10 Hz at 1% strain, and the nominal stiffness of each matrix was determined based on the value of the storage modulus at 1 Hz.

The HELP material allows independent selection of multiple biomaterial properties, allowing the study of organoid growth in response to different biochemical and biophysical matrix cues. Tuning these parameters allows the careful study of how cells in organoids respond to tissue mechanics. Indeed, the interplay of matrix stiffness, matrix stress relaxation, and matrix RGD content has been important in other engineered biomaterial systems. To explore these interactions within the HELP system, we first prepared a variant of our ELP protein that contains a non-integrin binding, sequence-scrambled peptide (RDG) that is known to be non-cell-adhesive. Next, by blending together RGD- and RDG-ELP proteins within the HELP matrix, we were able to tune the exact concentration of RGD ligands in our hydrogels from 0-1 mM without impacting the matrix mechanics (FIG. 4*a*, FIG. 10). To create matrices with a range of mechanical properties, we first varied the degree of hydrazine-benzaldehyde crosslinking (FIG. 4*b*, top) to create a stiff, elastic-like matrix (storage modulus, G'~1 kPa, termed "Stiff EL") and a more compliant, elastic matrix (G'~400 Pa, "Soft EL") (FIG. 4*c,d*). These matrices had equivalent, quasi-elastic stress relaxation profiles, with negligible stress relaxation over 60 mins and a stress-decay half-time ($t_{1/2}$) of about 18 hrs.

Figure 4:
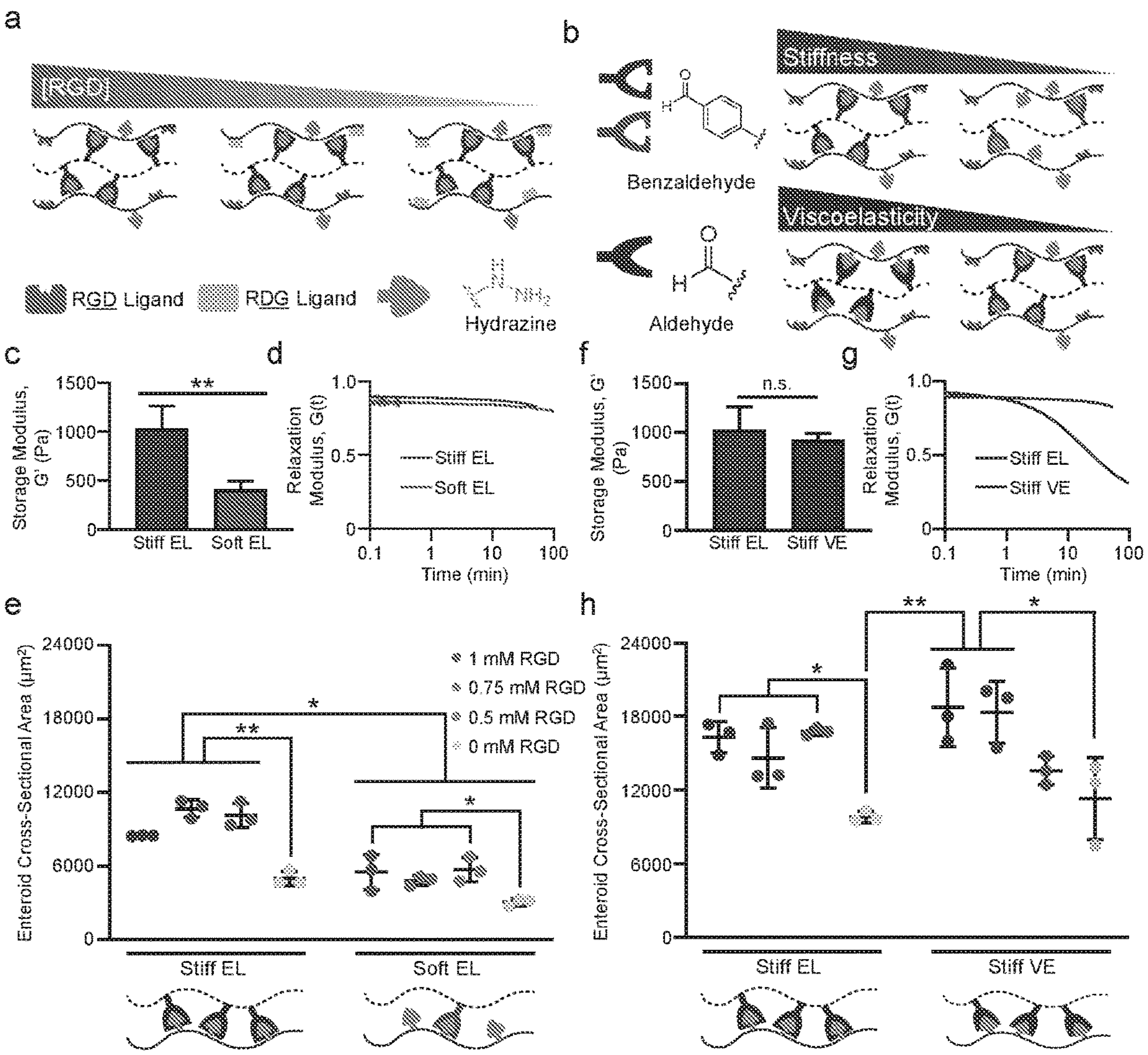
FIG. 4: Custom tailoring of HELP matrix properties. a) HELP schematic illustrating specification of the RGD ligand concentration by blending different ELP variants in the material. b) HELP schematic illustrating that matrix stiffness is modulated by changing the number of crosslinks (top), while matrix viscoelasticity is tuned by replacing benzaldehyde with aldehyde moieties. c) Shear storage moduli (G') of Stiff Elastic (EL) and Soft EL HELP matrices. Student's t-test, **=$p<0.01$, N=3-5. d) Step-strain stress relaxation curves comparing EL HELP formulations. e) Cross-sectional area measurements of enteroids in EL HELP materials at 12 days post-encapsulation. 2-way ANOVA with Tukey multiple comparisons testing, *=$p<0.05$, **=$p<0.01$, n=3. f) Shear storage moduli of Stiff EL and Stiff Viscoelastic (VE) formulations. Student's t-test, N=3-5, n.s.=not significant. g) Step-strain stress relaxation curves comparing Stiff EL and Stiff VE formulations. h) Cross-sectional area measurements of enteroids in stiff materials at 12 days post-encapsulation. 2-way ANOVA with Tukey multiple comparisons testing, *=$p<0.05$, **=$p<0.01$, n=3.
Figure 5:
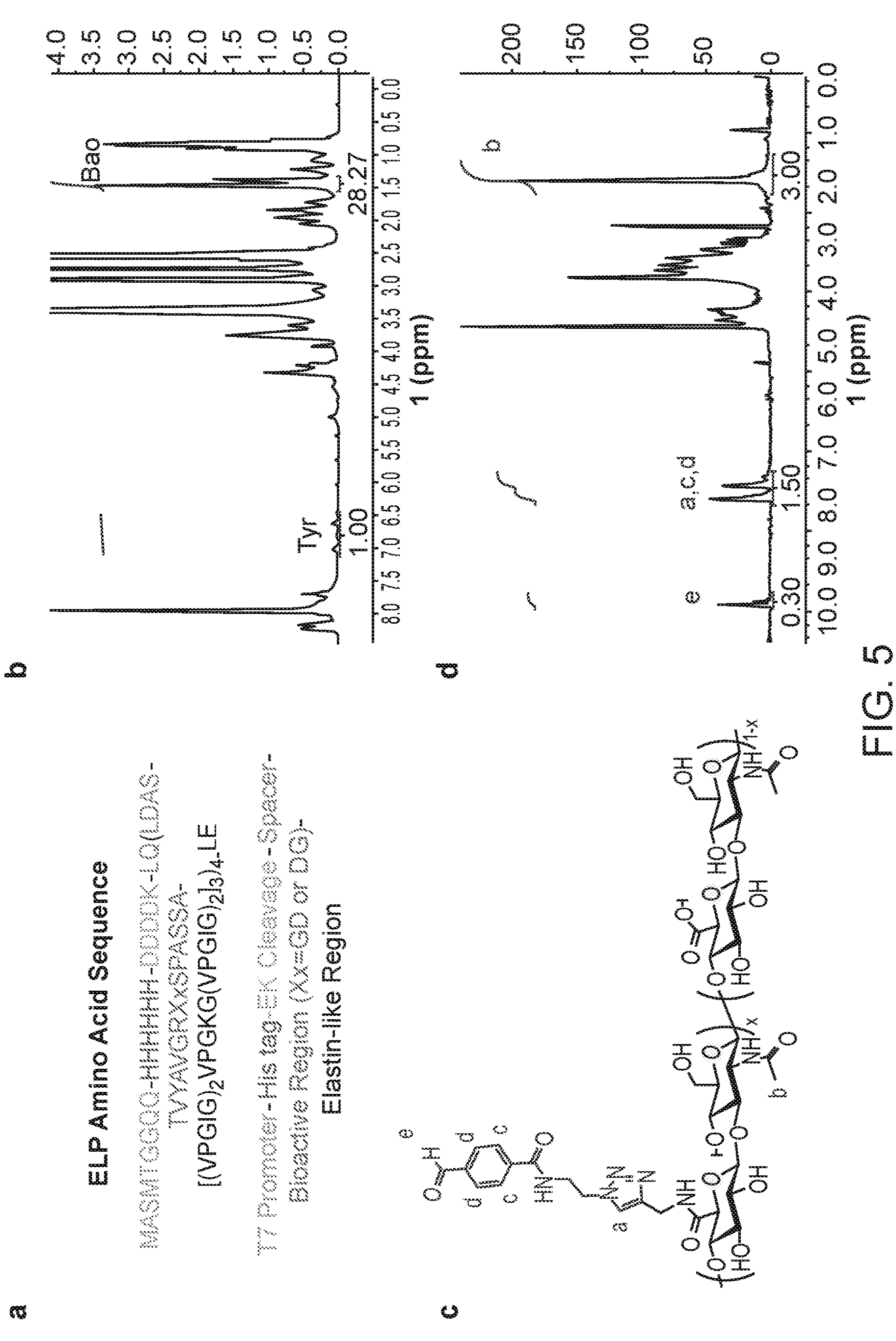
FIG. 5: HELP protein backbone and chemical modification. a) ELP amino acid sequence (SEQ ID NO:30) that can be modified to contain the fibronectin-mimicking RGD or scrambled RDG motifs. b) Nuclear magnetic resonance (NMR) of ELP modified with a hydrazine moiety. c) Hyaluronan structure modified with a benzaldehyde moiety. d) NMR of 30% modified hyaluronan with corresponding peaks from c. e) NMR of 12% modified hyaluronan with corresponding peaks from c.
Figure 5:
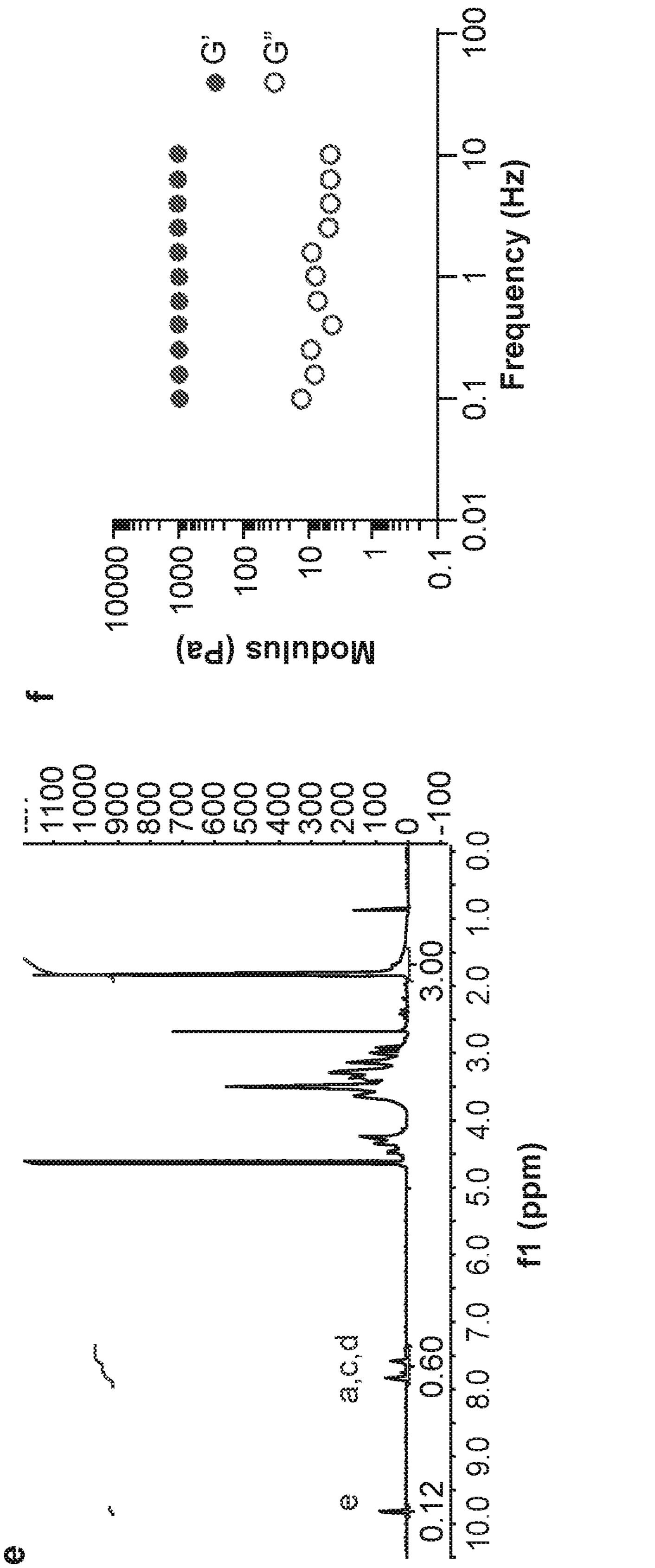
Figure 11:
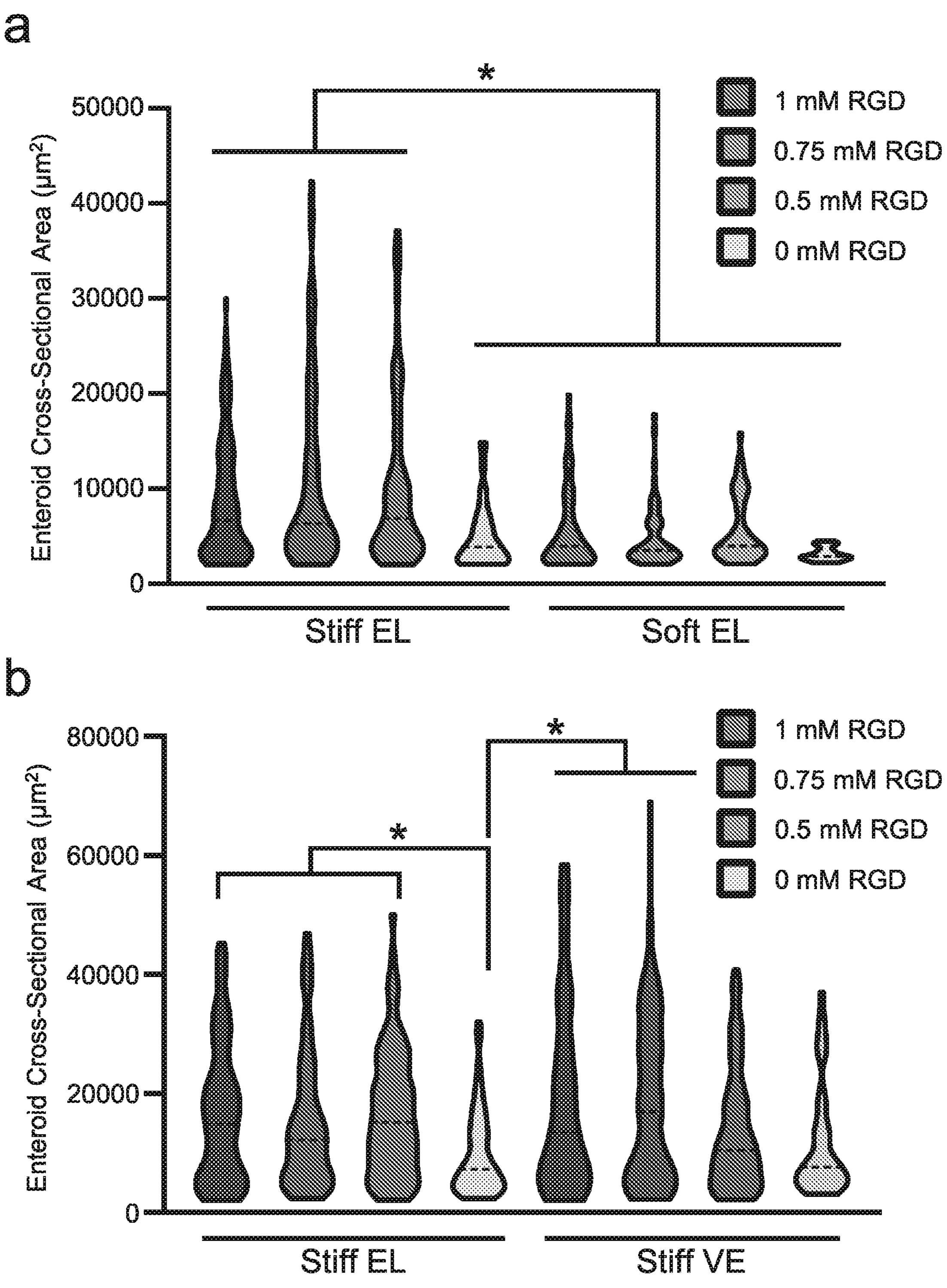
FIG. 11: Cross-sectional area of spheroids grown in distinct HELP formulations. a) Cross-sectional area of enteroids grown in Stiff EL compared to Soft EL HELP with varying concentrations of RGD ligand 12 days post-encapsulation. b) Cross-sectional area of enteroids grown in Stiff EL compared to Stiff VE HELP with varying concentrations of RGD ligand 12 days post-encapsulation. Kruskal-Wallis test with Dunn's multiple comparison test, *=$p<0.05$.
Figure 12:
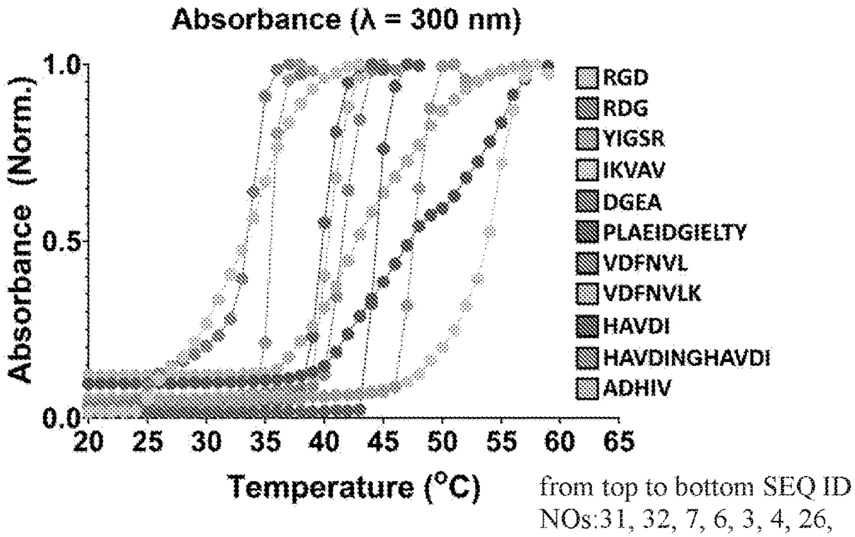
FIG. 12. Lower critical solution temperature characterization of engineered proteins designed for use in HELP gels. Six different variants of the engineered elastin-like protein (see Table 1) were synthesized, purified, and characterized for lower critical solution temperature behavior.
Figure 13:
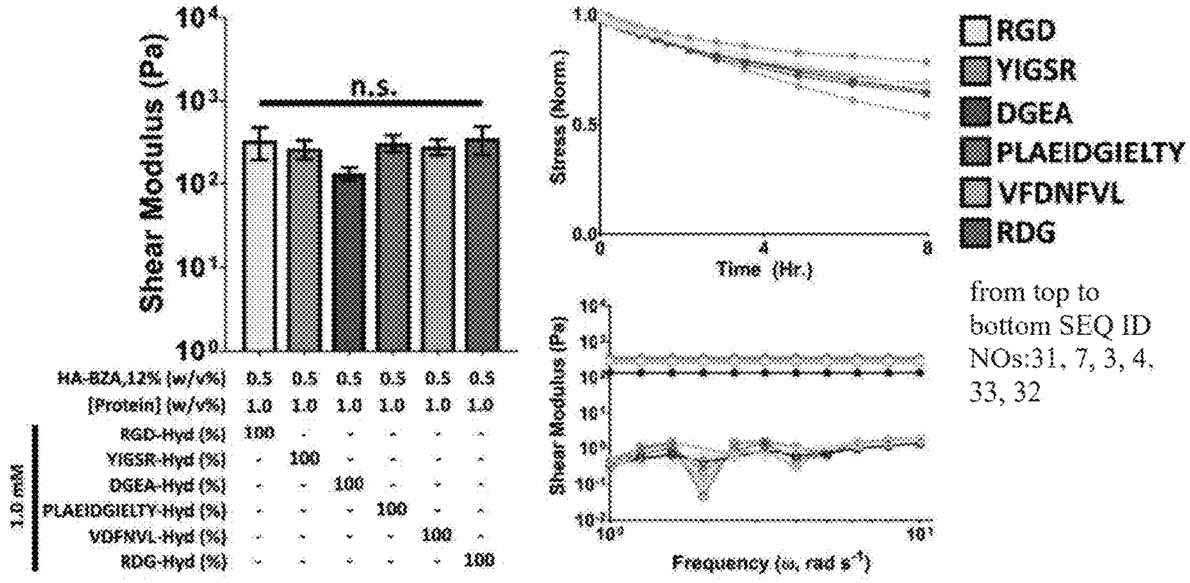
FIG. 13. To demonstrate modularity of these engineered proteins within the HELP system, six different variants of the engineered elastin-like protein (see Table 1) were modified with hydrazine groups and crosslinked with benzaldehyde-modified hyaluronic acid to form HELP gels that display six distinctly different bio-active peptide sequences. The six HELP gels were characterized for their viscoelastic properties by oscillatory rheology, demonstrating no statistically significant differences in their gel mechanics.
Figure 14:
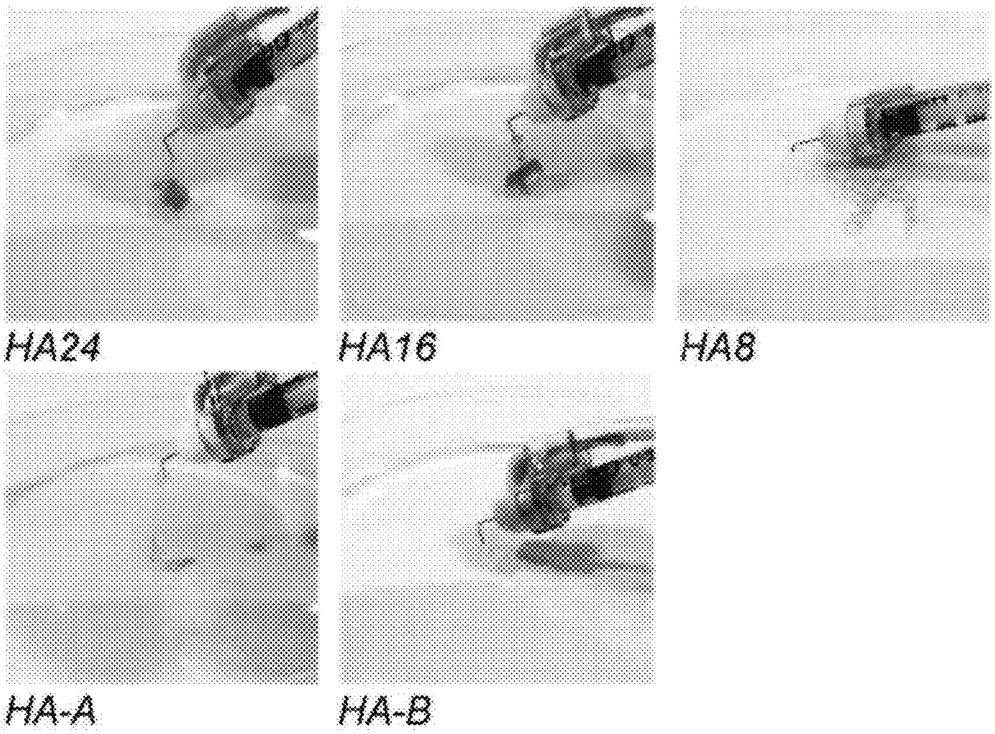
FIG. 14. By tuning the thermodynamic-averaged molecular weight between crosslinks, the overall polymer molecular weight, and the kinetics of the hydrazone crosslinks, the HELP gels can be formulated to be shear-thinning and hence injectable through a syringe needle or catheter upon application of force. Upon removal of force, the gel structure self-heals and recovers gel-phase mechanical properties. This cycle of extrusion and self-healing can be repeated multiple times. The gels are extrudable upon application of hand force through a variety of medical devices, including a 30-gauge syringe needle and a 150-cm catheter (0.75 mm diameter). The qualitative injectability of five HELP gels was tested by injecting each formulation through a hooked, 30-G insulin needle. (A) Injectability criteria included: (1) ability to be injectable after complete gelation (30 min), (2) injectable with one hand, and (3) no evidence of a sudden burst injection. (B) Qualitative stills taken from recordings of each injection. Each gel has been dyed with food coloring to improve visibility. (C) Table summarizing the qualitative assessment, where a check mark (✓) and a cross (x) signify passing or failing the test, respectively. Formulation HA-B was not injectable at all, and so criterions (2) and (3) could not be evaluated and have been designated with a (-).

We measured the distributions of patient-derived enteroid sizes as a function of varying material properties in sets of HELP matrices (data presented as means in FIG. 4, violin-plot distributions shown in FIG. 11). In general, the cross-sectional area of enteroids grown in stiffer gels (G'~1 kPa) were larger than those grown in softer gels (G'~400 Pa, FIG. 4*e*). This result is consistent with the stiffness range previously found to be optimal for murine as well as primary human intestinal organoids grown in synthetic PEG-based matrices. In addition to this trend, we observed that enteroids did not grow as robustly in matrices lacking the RGD ligand, independent of matrix stiffness. This is consistent with previous reports of intestinal organoids in synthetic matrices, where minimum threshold levels of RGD were required for optimum organoid growth. However, in these previous reports, organoids cultured in synthetic matrices without RGD were unable to form and remain viable. The fact that viable enteroids were formed in HELP matrices without the RGD ligand suggests that signaling from HA may be sufficient to induce some organoid formation, although co-presentation of RGD and HA resulted in significantly improved organoid growth (FIG. 4*e*).

We next explored the role of RGD concentration within matrices that were stress relaxing and viscoelastic. A matrix that is "stress relaxing" will undergo molecular-level remodeling to dissipate and relieve stress after it has been deformed by cellular forces. Work with other cell types has demonstrated that matrix stress relaxation may have even stronger effects on cell phenotype than matrix stiffness, and these effects vary with the integrin ligand concentration, since this is a primary mechanism that cells use to exert forces onto the matrix. Thus, we sought to design a family of biomimetic HELP matrices that enabled independent tuning of matrix stiffness, RGD ligand concentration, and matrix stress relaxation. A key feature of native extracellular matrices and EHS matrices is their ability to undergo stress relaxation due to their physical crosslinks, which can be easily remodeled. The remodeling kinetics of dynamic covalent crosslinks, such as those used in our HELP matrices, can be tuned through selection of the neighboring chemical moieties. By replacing a fraction of the benzaldehyde groups on HA with aldehyde groups (FIG. 4*b*, bottom), we formulated a faster stress relaxing ($t_{1/2}$~30 min), viscoelastic HELP matrix (termed "Stiff VE") with an identical stiffness as the quasi-elastic "Stiff EL" HELP matrix (FIG. 4*f,g*). Interestingly, we observed a greater dependence on RGD ligand concentration for enteroid growth in the viscoelastic gels compared to the elastic gels (FIG. 4*e,h*). The viscoelastic gels had a threshold of 0.75 mM RGD required for robust enteroid growth (FIG. 4*h*). These data suggest that in matrices capable of undergoing greater remodeling, enteroids may be more sensitive to the presence of integrin-ligands, while enteroids can more robustly form across a broader range of matrix properties in matrices with more elastic-like mechanics.

Figure 2:
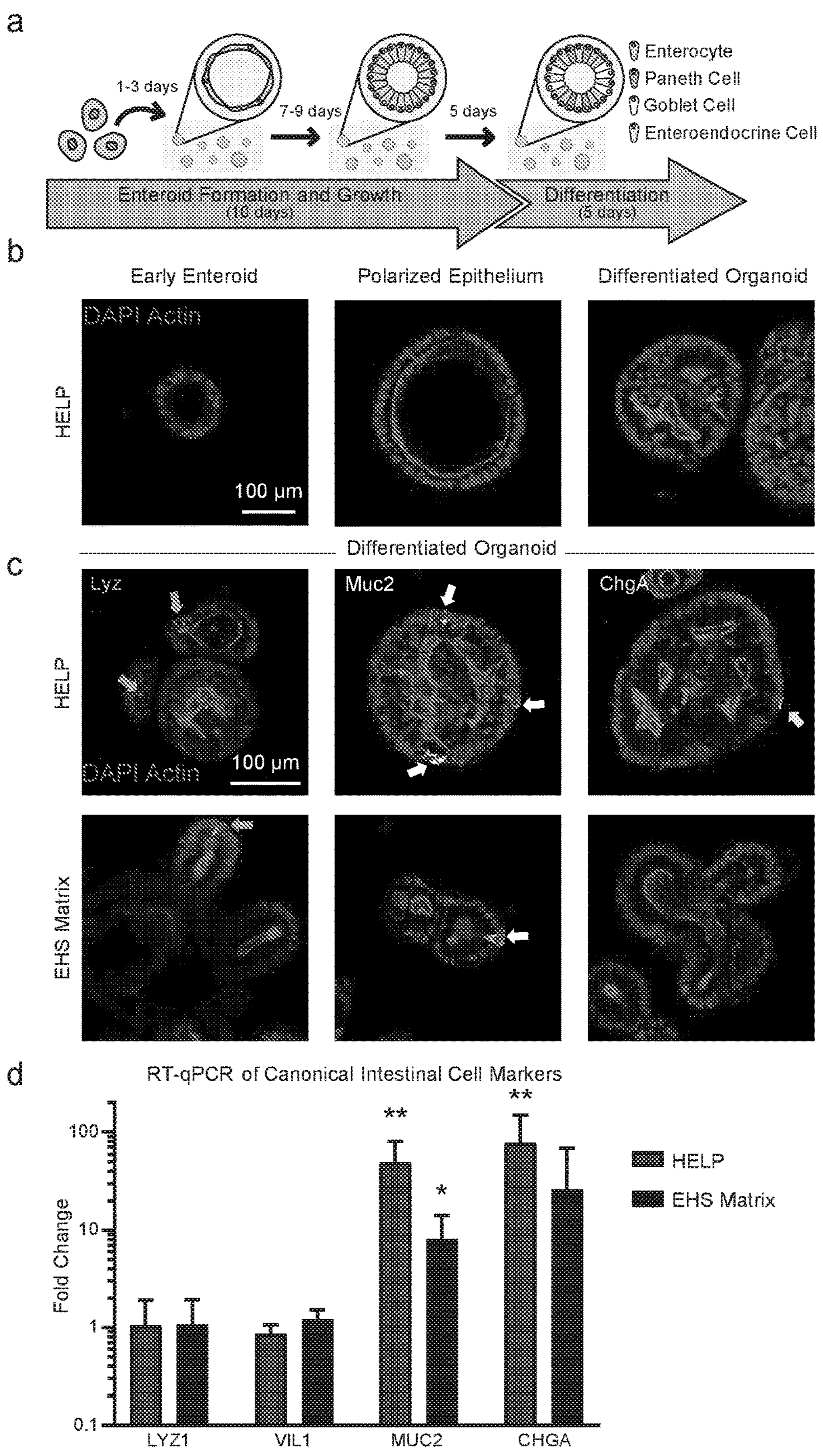
FIG. 2: Differentiation of organoids grown in HELP and EHS matrices. a) Schematic of differentiation experiment timeline. Organoids are cultured from single cells in growth medium for 10 days, followed by 5 days in differentiation medium (see Methods). b) Confocal micrographs illustrating the progression of organoids from early enteroid to polarized enteroid to differentiated organoid. c) Confocal micrographs demonstrating the observance of mature intestinal cell subtypes: Paneth cells ($Lyz^+$, left), goblet cells ($Muc2^+$, middle), and enteroendocrine cells ($ChgA^+$, right). d) RT-qPCR quantification of changes in RNA expression of differentiated cell type markers, compared to cells that were maintained for 15 days in maintenance medium, and relative to control gene BACT. Under the assumption that $C_T$ values are normally distributed, 2-tailed Student's t-tests were performed on $C_T$ values between differentiated vs. maintenance cultures. **=$p<0.01$, *=$p<0.05$, N=3 independent experiments, n=4 technical replicates.
Figure 3:
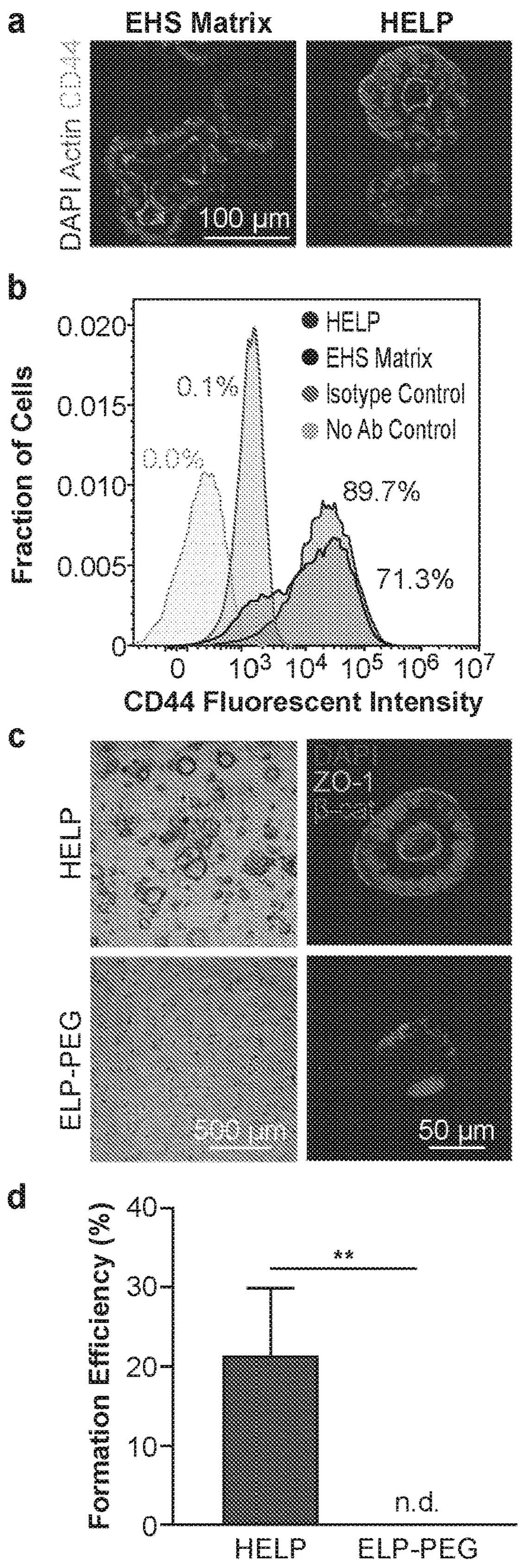
FIG. 3: Role of hyaluronan in HELP matrices. a) Comparative confocal micrographs of CD44 staining at the same intensity and gain settings in EHS and HELP matrices. b) Flow cytometric analysis of enteroids grown in EHS and HELP matrices 11 days post-encapsulation, compared to negative controls. c) Brightfield and confocal micrographs at 6 days post-seeding of enteroids grown in HELP and ELP-PEG matrices, where HA is absent in the ELP-PEG gels. d) Formation efficiency between enteroids grown in HELP and ELP-PEG. Data are mean+/−standard deviation, Student's t-test, **=$p<0.01$, n=3, n.d.=none detected.

In summary, here we present the HELP matrix that allows for the robust formation, growth, passaging, (FIG. 1) and differentiation (FIG. 2) of primary, human intestinal organoids from dissociated single cells. Interestingly, the presence of hyaluronan within HELP is sufficient to enable de novo enteroid formation from single cells, as ELP-only and ELP-PEG matrices with similar mechanics and RGD-ligand concentrations did not support enteroid formation (FIGS. 1, 3). We correlate this observation with an increase in expression of CD44, a well-known receptor for HA, in enteroids cultured in HELP matrices (FIG. 3). This receptor is known to be important in ISC renewal, thus our findings contribute to the collective understanding of matrix factors impacting intestinal cell proliferation and support further mechanistic study of designer matrices containing HA.

The HELP matrix is not only suitable for this specific cell source, but also supports murine intestinal organoids as well as human iPSC-derived hepatic organoids (FIG. 8). Thus, HELP matrices add to the emerging library of minimal matrices available for reproducible organoid culture. These results, combined with the bespoke tailoring of several material properties, including biochemical ligand density, matrix stiffness, and matrix stress relaxation rate (FIG. 4) position the HELP matrix as a platform that can be optimized for the culture of a wide variety of patient-derived organoids. Our well-defined, minimal, engineered matrix overcomes the key limitations of EHS matrices, notably batch-to-batch variability, insufficient tunability, biological complexity, and lack of clinical translatability, while avoiding the use of PEG. In the future, the HELP matrix could be customized to mimic patient-specific matrix properties, resulting in reproducible, personalized organoid cultures. By enabling the culture of human intestinal and other organoids, the HELP material has numerous future applications, including in studies of enteric disease pathology, developmental biology, and regenerative medicine.

Materials and Methods

Human Enteroid Passaging and Maintenance Culture in EHS Matrix. Human primary intestinal tissue was used between passages 4-24 for all experiments. Cells in maintenance cultures were maintained while encapsulated in 40 μL of EHS matrix, specifically Cultrex Basement Membrane Extract-Reduced Growth Factor (BME-RGF) Type 2 (Trevigen, Gaithersburg, MD) within 24-well plates. Enteroids were passaged every 1-2 weeks depending on growth rate. To passage enteroids, Cultrex droplets were flooded with ice-cold, 5 mM ethylenediamine tetraacetic acid (EDTA) in phosphate buffered saline (PBS) to dissolve the gel, centrifuged for 5 min at 500×g, treated with TrypLE (Thermo Fisher Scientific, Waltham, MA) for 10 min at 37° C., with vigorous mixing by pipette aspiration every 5 minutes to assist in the generation of single cells. The TrypLE was then quenched with enteroid growth medium (described below), and centrifuged for 5 min at 500×g. The pellet was washed in growth medium for cell counting, and then centrifuged for 5 min at 500×g. The cell pellet was resuspended in ice-cold Cultrex at a concentration of 750,000 cells/mL and transferred to the cell culture incubator. After 10 min of gelation at 37° C., 500 μL of pre-warmed growth medium was added to each well. Small molecule inhibitors, 10 μM Y-27632 and 2.5 μM CHIR-99021 (both obtained from Bio-Techne, Minneapolis, MN), were added to the medium for the first media change of maintenance cultures. Media was completely replaced every 3-4 days.

Mouse Enteroid Isolation and Culture. Murine intestinal enteroids were generated as described previously. Briefly, isolated murine small intestines were transected in the longitudinal direction, and washed with cold PBS. The tissue was then minced into roughly 5-mm square pieces and washed again with cold PBS. Tissue was then incubated in 2 mM EDTA in PBS on ice. Following this incubation, the EDTA solution was then aspirated, and tissue fragments were then mixed well with a 10-mL serological pipette using cold PBS, and the tissue was allowed to settle. The supernatant was discarded, and the sediment containing intestinal crypts was resuspended in PBS. Samples were vigorously mixed and then centrifuged for 5 min at 500×g, and then the crypt-rich supernatant was then passed through a 70-μm cell strainer (BD Biosciences, San Jose, CA). Crypts were centrifuged once more for 3 min at 200×g to separate out single cells. The fraction of mostly pure crypts was then used for culture.

Human Hepatic Organoid Differentiation and Culture. Hepatic organoids were generated as described previously. Briefly, normal iPSC derived secondary hepatic organoids (HO2) were digested in 0.25% trypsin-EDTA for 5 to 10 minutes. The cells were collected by centrifugation at 200 g for 3 minutes, resuspended in 25 μl of 1% HA, and directly mixed with preloaded 25 μl 1% ELP at 1,000 cells per well in a 24-well plate. After HELP solidification, 1 ml of growth media was added, and the cells were cultured for 6 days. The growth media consisted of RPMI plus B27 (Thermo Fisher Scientific, Waltham, MA) medium with the following growth factors: 250 nM LDN-193189, 3 μM CHIR99021, 10 μM A83-01, 100 ng/ml EGF, 10 ng/ml FGF10, and 20 ng/ml HGF. The cells were then cultured for 6 more days in a differentiation medium, which consisted of HCM (Lonza, Basel, SUI) medium supplemented with 10 μM DAPT, 10 ng/ml oncostatin M, 20 ng/ml HGF, 10 μM dexamethasone, and 10 ng/ml BMP4. To perform forskolin-induced swelling assay on HOs, both forskolin (FSK) and 3-isobutyl-1-methylxanthine (IBMX) (10 μM and 100 μM, respectively) were added to activate cAMP pathway and increase in CFTR (Cystic fibrosis transmembrane conductance regulator) function in HO culture for 24 hours. Swelling was visualized after staining with a 10-μM solution of the cell-permeable fluorescent dye calcein green. The difference in total area of each hepatic organoid after 24 hrs treatment was then calculated and plotted.

Intestinal Organoid Growth Medium Generation. Organoid growth base media consisted of a 1:1 mixture of ADMEM-F12 media (Thermo Fisher Scientific, Waltham, MA) and L-WRN (ATCC CRL3276) conditioned media. To generate L-WRN conditioned media, L-WRN cells were plated on T150 cell culture flasks in L-WRN growth medium (Dulbecco's Modified Essential Medium (DMEM) supplemented with 10% FBS and 1% penicillin-streptomycin-glutamine (PSQ)) and allowed to grow for 1-2 days. Growth media was changed and supplemented with L-WRN selection medium (L-WRN growth medium supplemented with 500 μg/mL each of G418 and hygromycin antibiotics to select for cells containing transgenic DNA encoding the secretion of Wnt-3A, R-spondin 3, and Noggin). Cells were grown until confluent, and split at a 1:4 ratio twice, and then split into multiple T150 flasks. Cells were cultured in L-WRN growth medium until confluent, washed with L-WRN collection medium (ADMEM-F12 with 10% FBS and 1% PSQ), and cultured for 24 h with fresh L-WRN collection medium. After 24 h, conditioned media was recovered from each flask and combined. Fresh L-WRN collection medium was replaced, and conditioned media generation and collection was repeated up to four times. ADMEM-F12 was mixed 1:1 with L-WRN conditioned media and supplemented with the following reagents: 1 mM HEPES (Thermo Fisher Scientific, Waltham, MA), 1× Glutamax (Thermo Fisher Scientific, Waltham, MA), 10 mM nicotinamide (Sigma-Aldrich, St. Louis, MO), 1 mM N-acetylcysteine (Sigma-Aldrich, St. Louis, MO), 1× B-27 supplement (Thermo Fisher Scientific, Waltham, MA), 0.5 μM A83-01 (Sigma-Aldrich, St. Louis, MO), 1× PSQ (Thermo Fisher Scientific, Waltham, MA), 10 nM Gastrin-I (Sigma-Aldrich, St. Louis, MO), 10 μM SB-202190 (Bio-Techne, Minneapolis, MN), 50 ng/mL recombinant EGF (Thermo Fisher Scientific, Waltham, MA), and 1× Normocin (InvivoGen, San Diego, CA).

Intestinal Organoid Differentiation. In order to differentiate intestinal enteroids into organoids, cells were maintained in growth medium for 10 days after encapsulation as single cells in HELP or EHS matrices, washed briefly with PBS, and switched into differentiation medium for 5 days of culture. Differentiation medium was Advanced DMEM/F12 medium supplemented with 1× Glutamax, 1× Penicillin/Streptomycin, 1× Normocin, 100 ng/mL recombinant noggin (Peprotech, Rocky Hill, NJ), 1× B27, 1 mM N-acetylcysteine, 50 ng/mL recombinant EGF, 10 nM gastrin-I, 10 μM Y-27632 ROCK inhibitor, 5 μM DAPT, and 500 nM A83-01.

ELP-Hydrazine Synthesis. Elastin-Like Protein (ELP) was prepared as described previously. Briefly, ELP sequences were cloned into pET15b plasmids, and a T7 promoter was used to control protein expression. BL21 (DE3)pLysS *Escherichia coli* (Life Technologies) containing ELP-encoding plasmids were cultured in Terrific Broth to an $OD_{600}$ of 0.8, and 1 mM isopropyl β-D-1-thiogalactopyranoside (IPTG) was used to induce expression. Bacteria were allowed to express protein for 7 h, and were subsequently harvested by centrifugation, suspended in TEN buffer (10 mM Tris, 1 mM EDTA, and 100 mM NaCl, pH 8.0), and lysed via three cycles of freeze-thaw. Cell lysate was treated with deoxyribonuclease (DNase) and 1 mM phenylmethanesulfonyl fluoride (PMSF) to inhibit proteolysis. ELP was purified by an alternating sequence of centrifugation steps at 4° C. and 37° C., followed by dialysis against deionized water for 4 shifts (48 h, 4 L volume per shift), then frozen at −80° C. and lyophilized. To modify ELP amines with hydrazine functional groups, lyophilized ELP (210 mg) was completely dissolved at 7 wt % in 3 mL of anhydrous dimethyl sulfoxide (DMSO) and then diluted to 3.5 wt % with 3 mL of anhydrous N,N-dimethylformamide (DMF). In a round-bottom flask, 3 mL of anhydrous DMF was used to separately dissolve tri-Boc-hydrazinoacetic acid (2 equiv:ELP amine), hexafluorophosphate azabenzotriazole tetramethyl uronium (HATU, 2 equiv:ELP amine), and 4-methylmorpholine (4.5 equiv:ELP amine), and this vessel was stirred for 5 min to allow HATU to activate the free acids on the tri-Boc-hydrazinoacetic acid. Next, the ELP solution was added to the round-bottom flask dropwise with stirring. The reaction was allowed to proceed overnight at room temperature (RT). The product was precipitated in ice-cold ether, centrifuged, and dried, yielding the Boc-protected ELP-hydrazine intermediate. This intermediate was analyzed by 1H NMR to quantify the modification efficiency (500 Hz, DMSO-d6) δ 7.00 (d, 2H), 6.62 (d, 2H), 1.46 (m, 27H). Modification efficiency was determined by comparing the integrated signal of the Boc protons (δ 1.5-1.35) to the aromatic protons of tyrosine residues on ELP (δ 7.00 and 6.62). To remove the Boc protecting groups, the ELP-hydrazine intermediate was dissolved at 2 wt % in 1:1 DCM:TFA with 2.5% v/v triisopropylsilane and stirred at RT for 4 h in a vented round-bottom flask. The product was precipitated in ether, centrifuged, and dried, then dissolved in DI water and dialyzed against DI water for 3 shifts (24 h, 4 L volume per shift), and lyophilized.

Hyaluronic Acid Modification. 100 kDa sodium hyaluronate (HA, Lifecore Biomedical, Chaska, MN, USA) was modified to have an aldehyde functional group by the following overall procedure: first the carboxylic acid groups on HA were amidated with propargylamine, generating an HA-alkyne intermediate; then, copper click chemistry was used to react this alkyne with the azide moiety of a heterobifunctional small molecule containing an aldehyde functional group onto the HA, generating HA functionalized with aldehydes.

HA-alkyne of 12% modification: HA was dissolved in 2-(N-morpholino)ethanesulfonic acid (MES) buffer (0.2 M, pH 4.5) to a concentration of 10 mg/mL. To this solution, N-hydroxysuccinimide (NHS, 0.8 eq. to the HA dimer unit), 1-ethyl-3-(3-dimethylaminopropyl) carbodiimide (EDC, 0.8 eq.), and propargyl amine (0.8 eq.) were added successively. After adjusting pH to 6, the mixture was stirred at RT for 4 h. The solution was then dialyzed against DI water for 6 shifts (3d, 4 L volume per shift) and lyophilized to give a white powder.

HA-alkyne of 30% modification: Sodium hyaluronate was dissolved in MES buffer (0.2 M, pH 4.5) to a concentration of 10 mg/mL. To this solution, NHS (1.5 eq. to the HA dimer unit), EDC (1.5 eq.), and propargyl amine (1.0 eq.) were added successively. After adjusting pH to 6, the mixture was stirred at RT for 4 h. The solution was then dialyzed against DI water for 6 shifts (3d, 4 L volume per shift) and lyophilized to give a white powder.

HA-alkynes were then modified by the following small molecule, 1, to generate HA-benzaldehyde. The small molecule was generated as follows:

1

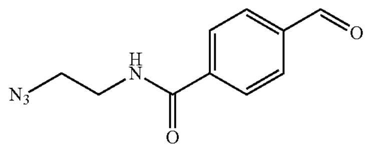

N-(2-azidoethyl)-4-formylbenzamide (1) was synthesized according to the method published in *Biomaterials,* 2018, 154, 213-222: HA was modified with molecule 1 according to previously reported procedure with minor modifications. HA-alkyne (300 mg) was dissolved in PBS at 2 wt % followed by the addition of 1 (1 eq. to HA dimer unit). A minimal amount of DMSO was used to dissolve 1 before it was added to the HA solution. The solution was then bubbled with $N_2$ for 30 min. Copper (II) sulfate pentahydrate (0.004 eq.) and sodium ascorbate (0.06 eq.) were dissolved in DI water, bubbled with $N_2$, and added to the HA solution. After stirring at RT for 1 d, the mixture was dialyzed against DI water for 3 d and lyophilized. Since the proton signals of aromatic rings on the benzaldeyde moiety overlap with triazole groups, the degree of modification on HA-benzaldehyde was quantified by integration of the proton signal (δ=7.5-8, 5H) relative to that of the methyl groups on N-acetylglucosamine of HA backbone (δ=1.8, 3H).

HA-aldehyde synthesis: HA-aldehyde was synthesized according to the method published in *Biomaterials,* 2009, 30, 2499-506: HA was first dissolved at 0.4 w/v % in Milli-Q water while stirring at room temperature. An aqueous solution of 0.1 M sodium periodate was added dropwise, and the reaction was stirred overnight at room temperature in the dark. The following day, ethylene glycol was added for 1 hr to inactivate any unreacted periodate. The solution was then purified by dialysis with a 10,000 MWCO membrane against Milli-Q water for 3 days, with fresh water changed in shifts of 12 hours. After dialysis, the dry product was obtained via freeze-drying.

Polyethylene glycol-benzaldehyde (PEG-BZA) synthesis: PEG-BZA was synthesized as previously described. Briefly, 4-formyl benzoic acid (0.528 g, 3.52 mmol, 2.1 eq. per amine; Sigma) was dissolved in 5 mL anhydrous dimethylformamide (DMF; Sigma) and activated with HATU (1.216 g, 3.2 mmol, 2 eq.; Sigma) and 4-methylmorpholine (0.792 mL, 7.2 mmol, 4.5 eq.; Sigma). The reaction was allowed to stir for 5 minutes before the addition of 4-arm 10 kDa PEG-amine (4 g, 0.2 mmol; Creative PEGworks) dissolved in 5 mL DMF for a total reaction volume of 10 mL. The reaction was allowed stir at room temperature overnight. The final polymer was precipitated in ethyl ether (Thermo Fisher), pelleted by centrifugation at 22,000 rcf for 20 minutes, and re-dissolved in Milli-Q water. PEG-BZA was dialyzed (MWCO: 3,500 Da; Spectrum) against Milli-Q water for 3 days at 4° C., and dialysis water was changed 2-3 times per day. PEG-BZA was lyophilized and stored at −20° C. Modification of PEG-BZA was estimated using $^1$H-NMR (500 MHz). PEG-BZA was dissolved in deuterated water ($D_2O$; Sigma) at 10 mg/mL. δ=9.9 ppm (1H, s, aldehyde); δ=7.93 and 7.82 ppm (2H each; d; benzene ring); δ=3.56 (217H per arm; s; PEG).

Engineered Hydrogel Formation and Rheological Characterization. Mechanical testing was performed on a stress-controlled ARG2 oscillatory rheometer (TA) using a 20-mm diameter, 1° cone-plate geometry with a 28-μm gap between the geometry and the rheometer stage. The two hydrogel components were dissolved separately at 2 wt % in PBS and kept on ice. First, 25 μL of the HA gel component was pipetted onto the middle of the rheometer stage, then 25 μL of the ELP component was pipetted directly into the droplet of HA, and the pipette tip was used to mix the components together. The rheometer head was promptly lowered, and the hydrogel components were allowed to react under 1 Hz, 1% strain oscillatory shear for 10 min at RT and 5 min at 37° C. This protocol was immediately followed by a frequency sweep from 0.1 to 10 Hz at 1% strain. The storage and loss moduli were taken to be the value at 1 Hz from these measurements. For stress relaxation measurements, samples were allowed to gel in situ for 10 min at RT and 10 min at 37° C. under 1 Hz, 1% oscillatory shear, and then a 5% step strain was applied. The stress relaxation response was measured for at least 45 min. The $t_{1/2}$ for each material was calculated as the time at which the stress had decayed to 50% of its stabilized initial value. Measurements were taken in at least triplicate.

Cell Encapsulation within Engineered Matrices. To form cell-laden HELP hydrogels, ELP and HA gel components were separately dissolved to form 2 w/v % stock solutions in PBS. To generate dissociated cultures, cells were passaged as described above, and the pellet was suspended in the ELP-hydrazine component and kept on ice. 3 μL of a selected modified HA component was added to the bottom of a 6 μL silicone mold (4 mm diameter, 0.5 mm height, plasma bonded to a 12-mm circular #1 coverglass). Then, 3 μL of the ELP-cell solution was pipetted directly into the droplet of modified HA. The pipette tip was then used to mix the two hydrogel components and homogeneously disperse the cells within the hydrogel. Hydrogels were allowed to crosslink for 10 min at room temperature and then 10 min at 37° C., after which 750 μL of growth medium was added. To form ELP-only gels, unmodified ELP protein was dissolved in PBS at a concentration of 3.25 w/v % at 4° C. A 5× solution of crosslinker tetrakis(hydroxymethyl)phosphonium chloride (THPC) was prepared by diluting 1:750 in PBS. Cells were passaged as described above, and the pellet was resuspended in the unmodified ELP component and kept on ice. ELP solution was then mixed with THPC at a 4:1 ELP:THPC volume ratio and mixed well by pipette aspiration before pipetting the ELP-THPC mixture into silicone-glass molds. ELP-only cultures were allowed to crosslink for 15 min at RT, followed by 15 min at 37° C. For ELP-PEG gels, enteroids were passaged as described above, and single cells were suspended in 4 w/v % ELP-hydrazine on ice. 3 μL of 8 w/v % PEG-BZA component was then pipetted onto the bottom of 6-μL silicone-glass molds while plates were kept on ice. 3 μL of ELP component with cells was then added to the PEG component and mixed by swirling with the pipette tip. These gels were then allowed to crosslink for 1 hr at 4° C., followed by 15 min at RT and 15 min at 37° C., followed by the addition of 750 μL of pre-warmed growth medium. For re-embedded cultures, enteroids in EHS matrices were incubated with 5 mM EDTA on ice for 45-60 min to completely dissociate the matrix, then centrifuged for 5 min at 500×g. Cells were then washed with growth medium and again centrifuged for 5 min at 500×g. To approximately keep cell seeding density consistent, cell counts from equivalent maintenance culture wells that had been dissociated into single cells were always conducted, and the assumption that equivalent volumes of maintenance culture had approximately equivalent numbers of cells was made to allow control of re-embedded enteroid seeding density. Growth medium was changed every 3-4 days. For all intestinal enteroid experiments, small molecule inhibitors Y-27632 and CHIR-99021 were not included in the media like they are for EHS maintenance cultures.

Enteroid Passaging in HELP Matrices. Enteroids in HELP were passaged every 10-14 days. To passage enteroids in HELP, the matrix was first degraded with 100 U/mL elastase from porcine pancreas (Thermo Fisher Scientific, Waltham, MA) and 2500 U/mL hyaluronidase from bovine testes (Sigma-Aldrich, St. Louis, MO) dissolved in PBS. Culture medium was completely aspirated from culture wells, including on the upper surface of the silicone molds. Once this upper surface was dried, a droplet of elastase-hyaluronidase mixture equal to the gel volume was added on top of the gel. The gels were incubated at 37° C. for 1 hr to allow for complete matrix degradation. Enteroids were then pipetted into a 15-mL conical centrifuge tube in an excess of growth medium to dilute the enzymes. Enteroids were spun down for 5 min at 500×g, and the pellet was then washed with growth medium and centrifuged once more for 5 min at 500×g. Enteroids were then passaged as described above, and single cells were encapsulated in HELP as described above.

Enteroid Formation and Growth Analysis. To analyze enteroid formation efficiency, up to 100 enteroids were analyzed per gel for 3 separate gels per condition. Within 4-6 hours after encapsulation in EHS matrix or HELP materials, the initial cell culture is observed under brightfield microscopy to ensure the presence of only single cells. Every 3 days, brightfield images of each well were taken at 10× magnification. For every well at each time point, 3 fields of view were randomly chosen, and 3 z-slices were taken in every field of view. To analyze enteroid growth, a Wacom Intuos tablet was used to trace the outlines of enteroids and quantify enteroid size using the Particle Analysis feature in FIJI (ImageJ, NIH). A enteroid formation threshold of 2000 $\mu m^2$ was selected based on previously reported enteroid morphology. A morphological criterion was also applied to separate viable enteroids from those that were severely misshapen. From this analysis, enteroid sizes and counts were collected for each well. Using the size of each image, and an approximated 250 μm z-volume for the 3 z-slices, organoid formation efficiency for each well was calculated by extrapolating the organoid count per z-stack volume in each well and comparing it to the initial cell seeding density, assuming uniform cell distribution. Formation efficiency for each condition was then calculated as an average of the 3 wells. To calculate average enteroid size, distribution statistics were generated for the pooled 3 wells. Outliers were excluded from data sets as follows:

Outlier>1.5*(Q3−Q1)+Q3, where Q3=$3^{rd}$ quartile of data and Q1=$1^{st}$ quartile of data. Average enteroid cross-sectional area was then calculated as the average of the 3 wells per condition.

Immunocytochemistry. To prepare samples for fixation, each well was washed briefly with pre-warmed PBS. Cells were fixed by adding 750 μL of pre-warmed 4% paraformaldehyde (PFA) with 0.1% glutaraldehyde in PBS and incubating at 37° C. for 30-45 min. Fixation solution was then aspirated and three 5-min washes of PBS were performed. Cells were permeabilized for 30 min with 0.25% v/v Triton X-100 in PBS (PBST), then blocked for 3 h in PBS with 5 wt % bovine serum albumin (BSA), 5% v/v goat serum, and 0.5% v/v Triton X-100. Primary antibody dilutions were prepared in PBS with 2.5 wt % BSA, 2.5% v/v goat serum, and 0.5% v/v Triton X-100 (Antibody Dilution Solution), and primary incubation was performed overnight at 4° C. Antibody solutions were removed, and 35-minute washes in PBST were performed. Secondary antibodies were diluted 1:500 in Antibody Dilution Solution and incubated overnight at 4° C. Secondary antibody solution was then removed and washed twice with PBST for 30 min each. 1:2000 dilution of DAPI and 1:250 dilution of phalloidin were prepared in PBST and incubated for 45 min, followed by three 5-min washes of PBST. Samples were then dried of excess liquid and inverted onto a droplet of ProLong Gold Antifade mounting medium on top of a rectangular coverglass. Mountant was allowed to cure for 48 h in the dark at RT before imaging on a DMI4000 B confocal microscope (Leica, Wetzlar, Germany).

TABLE 2

| Antibody Information | | | | |
|---|---|---|---|---|
| Target | Species | Vendor | Product # | Dilution |
| ZO-1 | Mouse | Thermo Fisher | 33-9100 | 1:150 |
| β-catenin | Rabbit | Cell Signaling | 8480 | 1:150 |
| Lysozyme | Rabbit | Thermo Fisher | PA5-16668 | 1:100 |
| Mucin-2 | Rabbit | Santa Cruz Biotechnology | SC-15334 | 1:50 |
| Chromogranin-A | Rabbit | Santa Cruz Biotechnology | SC-13090 | 1:50 |
| CD44 | Mouse | Santa Cruz Biotechnology | SC-7297 | 1:50 |
| Ki67 | Rabbit | Santa Cruz Biotechnology | SC-15402 | 1:100 |
| HNF4α | Goat | Santa Cruz Biotechnology | SC-6556 | 1:100 |
| Cytokeratin 19 | Mouse | DAKO | M088801-2 | 1:50 |
| Keratin 8 | Rat | Dev. Studies Hybridoma Bank (DSHB) | TROMA-I | 1:200 |

Quantitative real-time RT-PCR Analysis. Hydrogels were removed from silicone molds using a pipette tip to scrape and transfer the gels into 1.5-mL Eppendorf tubes containing 500 μL of Trizol reagent (Invitrogen, Carlsbad, CA) on ice to extract RNA. The solution was then sonicated to allow complete break-up of hydrogels for optimal RNA extraction. Phenol-chloroform extraction was used to isolate RNA with Phase Lock Gels (Quantabio, Beverly, MA). A constant amount of RNA (0.1-1 μg) was reverse transcribed using the High-Capacity cDNA Reverse Transcription Kit (Applied Biosystems, Foster City, CA). 1 μg of cDNA in 5 μL of nuclease free water was then mixed with 10 μL of Fast SYBR Green Master Mix (Applied Biosystems, Foster City, CA) and run on the Applied Biosystems StepOnePlus Real Time PCR System. Primers used in this work are listed in Table S2.

TABLE S2-PCR

| Primers | | |
|---|---|---|
| Target/GENE | Forward Primer (5'-3') | Reverse Primer (5'-3') |
| Villin-1/VIL1 | CTGAGCGCCCAAGTCAAAG (SEQ ID NO: 37) | AGCAGTCACCATCGAAGAAGC (SEQ ID NO: 42) |
| Mucin-2/MUC2 | GAGGGCAGAACCCGAAACC (SEQ ID NO: 38) | GGCGAAGTTGTAGTCGCAGAG (SEQ ID NO: 43) |
| Lysozyme/LYZ1 | TCAATAGCCGCTACTGGTGTA (SEQ ID NO: 39) | ATCACGGACAACCCTCTTTGC (SEQ ID NO: 44) |
| Chromogranin A/ CHGA | AGAATTTACTGAAGGAGCTCCA AG (SEQ ID NO: 40) | TCCTCTCTTTTCTCCATAACAT CC (SEQ ID NO: 45) |
| ß-actin/ACTB | CATGTACGTTGCTATCCAGGC (SEQ ID NO: 41) | CTCCTTAATGTCACGCACGAT (SEQ ID NO: 46) |

Flow Cytometric Analysis. Enteroids were dissociated into single cells following the methods outlined above (see Human Organoid Passaging and Maintenance Culture in EHS Matrix and Enteroid Passaging in HELP Matrices). The cells were centrifuged for 5 min at 500×g to pellet. The media was then removed from each pellet and the cells were resuspended in FACS buffer (PBS+1 mM EDTA [Invitrogen]+2% v/v FBS [Atlanta Bio]+1% penicillin/streptomycin [Gibco]) supplemented with fluorophore-conjugated primary antibodies [BioLegend anti-human CD44 antibody, BioLegend IgG2B isotype control]. Antibody staining was performed for 30 min at 4° C. in the dark. Following staining, the cells were washed twice using FACS buffer and resuspended in 200 μL FACS buffer with DAPI (1:10,000, BioLegend) to select for live cells. Flow cytometry was performed on a Beckman Coulter CytoFlex analyzer (Stanford Stem Cell Institute FACS Core). To analyze the data, gates were determined using forward and side scatter with height and width used to identify cell doublets. Subsequently, live DAPI-negative cells were gated for all marker analyses and population frequency calculations.

Statistical Analysis. The following statistical significance representation is used for all significance testing in this publication: *, #=$p<0.05$, =$p<0.01$, *=$p<0.001$, **=$p<0.0001$. Data from FIGS. 1***g* and S3 were analyzed by 1-way ANOVA with Tukey post-hoc testing to compare individual means. The data from FIG. 2*d* was analyzed via unpaired, 2-tailed Student's t-test to compare gene expression changes between undifferentiated and differentiated conditions for each material. The data from FIGS. 3*d*, 4*c*, 4*f*, and S4 were analyzed using a 2-tailed Student's t-test. The data from FIGS. 4*e* and 4*h* were analyzed by 2-way ANOVA with Tukey post-hoc testing to compare individual means. The data in Figure S7 were analyzed using a Kruskal-Wallis test with Dunn's multiple comparison test. All statistical analysis was performed using Graph Pad Prism 8.0 software (GraphPad Software, La Jolla, CA, USA).

REFERENCES

1. Bar-Ephraim, Y. E., Kretzschmar, K. & Clevers, H. Organoids in immunological research. *Nat. Rev. Immunol.* (2019). doi:10.1038/s41577-019-0248-y
2. Huch, M., Knoblich, J. A., Lutolf, M. P. & Martinez-Arias, A. The hope and the hype of organoid research. *Dev.* 144, 938-941 (2017).
3. Rossi, G., Manfrin, A. & Lutolf, M. P. Progress and potential in organoid research. *Nature Reviews Genetics* (2018). doi:10.1038/s41576-018-0051-9
4. Sato, T. et al. Single Lgr5 stem cells build crypt-villus structures in vitro without a mesenchymal niche. *Nature* 459, 262-265 (2009).
5. Ootani, A. et al. Sustained in vitro intestinal epithelial culture within a Wnt-dependent stem cell niche. *Nat. Med.* 15, 701-706 (2009).
6. Kratochvil, M. J. et al. Engineered materials for organoid systems. *Nat. Rev. Mater.* 4, 606-622 (2019).
7. Gjorevski, N. et al. Designer matrices for intestinal stem cell and organoid culture. *Nature* 539, 560-564 (2016).
8. Cruz-Acuña, R. et al. Synthetic hydrogels for human intestinal organoid generation and colonic wound repair. *Nat. Cell Biol.* 19, 1326-1335 (2017).
9. DiMarco, R. L., Dewi, R. E., Bernal, G., Kuo, C. & Heilshorn, S. C. Protein-engineered scaffolds for in vitro 3D culture of primary adult intestinal organoids. *Biomater. Sci.* 3, 1376-1385 (2015).
10. Hushka, E. A., Yavitt, F. M., Brown, T. E., Dempsey, P. J. & Anseth, K. S. Relaxation of Extracellular Matrix Forces Directs Crypt Formation and Architecture in Intestinal Organoids. *Adv. Healthc. Mater.* 1901214, 1-9 (2020).
11. Chen, Y., Zhou, W., Roh, T., Estes, M. K. & Kaplan, D. L. In vitro enteroid-derived three-dimensional tissue model of human small intestinal epithelium with innate immune responses. *PLoS One* 12, 1-20 (2017).
12. Hernandez-Gordillo, V. et al. Fully synthetic matrices for in vitro culture of primary human intestinal enteroids and endometrial organoids. *Biomaterials* 254, 120125 (2020).
13. Rezakhani, S., Gjorevski, N. & Lutolf, M. P. Low-Defect Thiol-Michael Addition Hydrogels as Matrigel Substitutes for Epithelial Organoid Derivation. *Adv. Funct. Mater.* 2000761, 2000761 (2020).
14. Garay, R. P., El-Gewely, R., Armstrong, J. K., Garratty, G. & Richette, P. Antibodies against polyethylene glycol in healthy subjects and in patients treated with PEG-conjugated agents. *Expert Opin. Drug Deliv.* 9, 1319-1323 (2012).
15. Zhang, P., Sun, F., Liu, S. & Jiang, S. Anti-PEG antibodies in the clinic: Current issues and beyond PEGylation. *J. Control. Release* (2016). doi:10.1016/j.jconrel.2016.06.040
16. Wang, L., Murthy, S. K., Fowle, W. H., Barabino, G. A. & Carrier, R. L. Influence of micro-well biomimetic topography on intestinal epithelial Caco-2 cell phenotype. *Biomaterials* 30, 6825-6834 (2009).
17. Benoit, Y. D., Groulx, J.-F., Gagné, D. & Beaulieu, J.-F. RGD-Dependent Epithelial Cell-Matrix Interactions in the Human Intestinal Crypt. *J. Signal Transduct.* 2012, 1-10 (2012).
18. Gracz, A. D. et al. Brief Report: CD24 and CD44 mark human intestinal epithelial cell populations with characteristics of active and facultative stem cells. *Stem Cells* 31, 2024-2030 (2013).
19. Itzkovitz, S. et al. Single-molecule transcript counting of stem-cell markers in the mouse intestine. *Nat. Cell Biol.* 14, 106-114 (2012).
20. Riehl, T. E., Foster, L. & Stenson, W. F. Hyaluronic acid is radioprotective in the intestine through a TLR4 and COX-2-mediated mechanism. *AJP Gastrointest. Liver Physiol.* 302, G309-G316 (2012).
21. Fevr, T., Robine, S., Louvard, D. & Huelsken, J. Wnt/-Catenin Is Essential for Intestinal Homeostasis and Maintenance of Intestinal Stem Cells. *Mol. Cell. Biol.* 27, 7551-7559 (2007).
22. De La Motte, C. A. & Kessler, S. P. The role of hyaluronan in innate defense responses of the intestine. *International Journal of Cell Biology* 2015, (2015).
23. Kim, M. S. et al. An in vivo study of the host tissue response to subcutaneous implantation of PLGA- and/or porcine small intestinal submucosa-based scaffolds. *Biomaterials* 28, 5137-5143 (2007).
24. Wang, H. et al. Covalently Adaptable Elastin-Like Protein—Hyaluronic Acid (ELP—HA) Hybrid Hydrogels with Secondary Thermoresponsive Crosslinking for Injectable Stem Cell *Delivery. Adv. Funct. Mater.* 27, (2017).
25. Lou, J., Stowers, R., Nam, S., Xia, Y. & Chaudhuri, O. Stress relaxing hyaluronic acid-collagen hydrogels promote cell spreading, fiber remodeling, and focal adhesion formation in 3D cell culture. *Biomaterials* 154, 213-222 (2018).

26. Lou, J. et al. Dynamic Hyaluronan Hydrogels with Temporally Modulated High Injectability and Stability Using a Biocompatible Catalyst. *Adv. Mater.* 30, 1-6 (2018).

27. McKinnon, D. D., Domaille, D. W., Cha, J. N. & Anseth, K. S. Biophysically defined and cytocompatible covalently adaptable networks as viscoelastic 3d cell culture systems. *Adv. Mater.* 26, 865-872 (2014).

28. Chaudhuri, O. et al. Hydrogels with tunable stress relaxation regulate stem cell fate and activity. *Nat. Mater.* 15, 326-333 (2015).

29. Straley, K. S. & Heilshorn, S. C. Independent tuning of multiple biomaterial properties using protein engineering. *Soft Matter* 5, 114 (2009).

30. Rosales, A. M. & Anseth, K. S. The design of reversible hydrogels to capture extracellular matrix dynamics. *Nat. Rev. Mater.* 1, 1-16 (2016).

31. Wang, H. & Heilshorn, S. C. Adaptable Hydrogel Networks with Reversible Linkages for Tissue Engineering. *Adv. Mater.* 27, 3717-3736 (2015).

32. Bökel, C. & Brown, N. H. Integrins in development: Moving on, responding to, and sticking to the extracellular matrix. *Developmental Cell* (2002). doi:10.1016/S1534-5807(02)00265-4

33. Sheetz, M. P., Felsenfeld, D. P. & Galbraith, C. G. Cell migration: regulation of force on extracellular-complexes. *Trends Cell Biol.* 8, 51-54 (1998).

34. Roca-Cusachs, P. et al. Integrin-dependent force transmission to the extracellular matrix by α-actinin triggers adhesion maturation. *Proc. Natl. Acad. Sci. U.S.A* 110, (2013).

35. Tan, S. J. et al. Regulation and dynamics of force transmission at individual cell-matrix adhesion bonds. *Sci. Adv.* 6, 1-12 (2020).

36. Chaudhuri, O. et al. Hydrogels with tunable stress relaxation regulate stem cell fate and activity. *Nat. Mater.* 15, 326-334 (2016).

37. McKinnon, D. D., Domaille, D. W., Cha, J. N. & Anseth, K. S. Bis-aliphatic hydrazone-linked hydrogels form most rapidly at physiological pH: Identifying the origin of hydrogel properties with small molecule kinetic studies. *Chem. Mater.* (2014).

What is claimed is:

1. A two-component hydrogel matrix system comprising: a first component comprising a defined ratio of hyaluronic acid (HA) modified to comprise a pendant reactant group benzaldehyde; and a second component comprising an elastin-like protein (ELP) modified to comprise a pendant reactant group hydrazine group; wherein cross-links between the first component and the second component are formed to generate a hydrogel upon mixing.

2. The system of claim 1, wherein matrix stiffness is independently tuned by varying the ratio of the reactant groups present on the first component, to reactant groups present on the second component.

3. The system of claim 1, wherein the ratio of reactant groups is varied by one or more of: specifying the number of reactant groups on HA; specifying the number of reactant groups on ELP; and specifying the ratio of HA:ELP.

4. The system of claim 1, wherein the ELP comprises from 1 to 7 elastin-like motifs.

5. The system of claim 4, wherein the elastin-like motifs are selected from SEQ ID NO:23, 24 and 25.

6. The system of claim 1, wherein the ELP comprises a cell adhesive domain from 15 to 45 amino acids in length, comprising one or more cell adhesion sequence motifs, or scrambled or lacking RGD.

7. The system of claim 6, wherein the cell adhesion motifs are selected from RGD or any of SEQ ID NO:3 to SEQ ID NO:9.

8. The system of claim 1, wherein the ELP comprises one or both of SEQ ID NO: 1 and SEQ ID NO:2.

9. The system of claim 1, wherein the cell-adhesive peptide concentration of the hydrogel is tuned by varying the ratio of ELP comprising a cell adhesive motif to ELP lacking a cell-adhesive motif.

10. The system of claim 7, wherein the ratio of ELP comprising a cell adhesive motif to ELP lacking a cell-adhesive motif is from 100:0 to 0:100.

11. The system of claim 1, wherein the ELP comprises from 3 to 20 hydrazine groups.

12. The system of claim 1, wherein the hydrogel comprises up to about 1.5 mM RGD.

13. A hydrogel formed from the system of claim 1.

14. A method of culturing a mammalian cell, the method comprising encapsulating an initiating population of mammalian cells in a hydrogel of claim 13, and maintaining the encapsulated cells in a suitable medium.

15. The method of claim 14, wherein the initiating cell population comprises a single cell suspension or a tissue explant.

16. The method of claim 14, wherein the cell population comprises stem cells.

17. The method of claim 14, wherein the initiating cell population differentiates into organoids in culture.

18. The method claim 14, wherein encapsulated cells are passaged by enzymatically degrading the hydrogel.

19. The system of claim 1, wherein the molecular weight of the HA is from 20 kDa to 100 kDa.

20. The method of claim 16, wherein the stem cells comprise epithelial cells.

* * * * *

SEQUENCE LISTING

```
<160> NUMBER OF SEQ ID NOS: 46

<210> SEQ ID NO 1
<211> LENGTH: 378
<212> TYPE: PRT
<213> ORGANISM: Artificial sequence
<220> FEATURE:
<223> OTHER INFORMATION: synthetic sequence

<400> SEQUENCE: 1

Leu Gln Leu Asp Ala Ser Thr Val Tyr Ala Val Gly Arg Gly Asp Ser
1               5                   10                  15

Pro Ala Ser Ser Ala Val Pro Gly Ile Gly Val Pro Gly Ile Gly Val
            20                  25                  30

Pro Gly Lys Gly Val Pro Gly Ile Gly Val Pro Gly Ile Gly Val Pro
        35                  40                  45

Gly Ile Gly Val Pro Gly Ile Gly Val Pro Gly Lys Gly Val Pro Gly
    50                  55                  60

Ile Gly Val Pro Gly Ile Gly Val Pro Gly Ile Gly Val Pro Gly Ile
65                  70                  75                  80

Gly Val Pro Gly Lys Gly Val Pro Gly Ile Gly Val Pro Gly Ile Gly
                85                  90                  95

Leu Asp Ala Ser Thr Val Tyr Ala Val Gly Arg Gly Asp Ser Pro Ala
            100                 105                 110

Ser Ser Ala Val Pro Gly Ile Gly Val Pro Gly Ile Gly Val Pro Gly
        115                 120                 125

Lys Gly Val Pro Gly Ile Gly Val Pro Gly Ile Gly Val Pro Gly Ile
    130                 135                 140

Gly Val Pro Gly Ile Gly Val Pro Gly Lys Gly Val Pro Gly Ile Gly
145                 150                 155                 160

Val Pro Gly Ile Gly Val Pro Gly Ile Gly Val Pro Gly Ile Gly Val
                165                 170                 175

Pro Gly Lys Gly Val Pro Gly Ile Gly Val Pro Gly Ile Gly Leu Asp
            180                 185                 190

Ala Ser Thr Val Tyr Ala Val Gly Arg Gly Asp Ser Pro Ala Ser Ser
        195                 200                 205

Ala Val Pro Gly Ile Gly Val Pro Gly Ile Gly Val Pro Gly Lys Gly
```

-continued

```
    210                 215                 220

Val Pro Gly Ile Gly Val Pro Gly Ile Gly Val Pro Gly Ile Gly Val
225                 230                 235                 240

Pro Gly Ile Gly Val Pro Gly Lys Gly Val Pro Gly Ile Gly Val Pro
                245                 250                 255

Gly Ile Gly Val Pro Gly Ile Gly Val Pro Gly Ile Gly Val Pro Gly
            260                 265                 270

Lys Gly Val Pro Gly Ile Gly Val Pro Gly Ile Gly Leu Asp Ala Ser
        275                 280                 285

Thr Val Tyr Ala Val Gly Arg Gly Asp Ser Pro Ala Ser Ser Ala Val
    290                 295                 300

Pro Gly Ile Gly Val Pro Gly Ile Gly Val Pro Gly Lys Gly Val Pro
305                 310                 315                 320

Gly Ile Gly Val Pro Gly Ile Gly Val Pro Gly Ile Gly Val Pro Gly
                325                 330                 335

Ile Gly Val Pro Gly Lys Gly Val Pro Gly Ile Gly Val Pro Gly Ile
            340                 345                 350

Gly Val Pro Gly Ile Gly Val Pro Gly Ile Gly Val Pro Gly Lys Gly
        355                 360                 365

Val Pro Gly Ile Gly Val Pro Gly Ile Gly
    370                 375


<210> SEQ ID NO 2
<211> LENGTH: 378
<212> TYPE: PRT
<213> ORGANISM: Artificial sequence
<220> FEATURE:
<223> OTHER INFORMATION: synthetic sequence

<400> SEQUENCE: 2

Leu Gln Leu Asp Ala Ser Thr Val Tyr Ala Val Gly Arg Asp Gly Ser
1               5                   10                  15

Pro Ala Ser Ser Ala Val Pro Gly Ile Gly Val Pro Gly Ile Gly Val
            20                  25                  30

Pro Gly Lys Gly Val Pro Gly Ile Gly Val Pro Gly Ile Gly Val Pro
        35                  40                  45

Gly Ile Gly Val Pro Gly Ile Gly Val Pro Gly Lys Gly Val Pro Gly
    50                  55                  60

Ile Gly Val Pro Gly Ile Gly Val Pro Gly Ile Gly Val Pro Gly Ile
65                  70                  75                  80

Gly Val Pro Gly Lys Gly Val Pro Gly Ile Gly Val Pro Gly Ile Gly
                85                  90                  95

Leu Asp Ala Ser Thr Val Tyr Ala Val Gly Arg Asp Gly Ser Pro Ala
            100                 105                 110

Ser Ser Ala Val Pro Gly Ile Gly Val Pro Gly Ile Gly Val Pro Gly
        115                 120                 125

Lys Gly Val Pro Gly Ile Gly Val Pro Gly Ile Gly Val Pro Gly Ile
    130                 135                 140

Gly Val Pro Gly Ile Gly Val Pro Gly Lys Gly Val Pro Gly Ile Gly
145                 150                 155                 160

Val Pro Gly Ile Gly Val Pro Gly Ile Gly Val Pro Gly Ile Gly Val
                165                 170                 175

Pro Gly Lys Gly Val Pro Gly Ile Gly Val Pro Gly Ile Gly Leu Asp
            180                 185                 190

Ala Ser Thr Val Tyr Ala Val Gly Arg Asp Gly Ser Pro Ala Ser Ser
```

-continued

```
        195                 200                 205

Ala Val Pro Gly Ile Gly Val Pro Gly Ile Gly Val Pro Gly Lys Gly
    210                 215                 220

Val Pro Gly Ile Gly Val Pro Gly Ile Gly Val Pro Gly Ile Gly Val
225                 230                 235                 240

Pro Gly Ile Gly Val Pro Gly Lys Gly Val Pro Gly Ile Gly Val Pro
                245                 250                 255

Gly Ile Gly Val Pro Gly Ile Gly Val Pro Gly Ile Gly Val Pro Gly
            260                 265                 270

Lys Gly Val Pro Gly Ile Gly Val Pro Gly Ile Gly Leu Asp Ala Ser
        275                 280                 285

Thr Val Tyr Ala Val Gly Arg Asp Gly Ser Pro Ala Ser Ser Ala Val
    290                 295                 300

Pro Gly Ile Gly Val Pro Gly Ile Gly Val Pro Gly Lys Gly Val Pro
305                 310                 315                 320

Gly Ile Gly Val Pro Gly Ile Gly Val Pro Gly Ile Gly Val Pro Gly
                325                 330                 335

Ile Gly Val Pro Gly Lys Gly Val Pro Gly Ile Gly Val Pro Gly Ile
            340                 345                 350

Gly Val Pro Gly Ile Gly Val Pro Gly Ile Gly Val Pro Gly Lys Gly
        355                 360                 365

Val Pro Gly Ile Gly Val Pro Gly Ile Gly
    370                 375


<210> SEQ ID NO 3
<211> LENGTH: 4
<212> TYPE: PRT
<213> ORGANISM: Artificial sequence
<220> FEATURE:
<223> OTHER INFORMATION: synthetic sequence

<400> SEQUENCE: 3

Asp Gly Glu Ala
1


<210> SEQ ID NO 4
<211> LENGTH: 12
<212> TYPE: PRT
<213> ORGANISM: Artificial sequence
<220> FEATURE:
<223> OTHER INFORMATION: synthetic sequence

<400> SEQUENCE: 4

Pro Leu Ala Glu Ile Asp Gly Ile Glu Leu Thr Tyr
1               5                   10


<210> SEQ ID NO 5
<211> LENGTH: 8
<212> TYPE: PRT
<213> ORGANISM: Artificial sequence
<220> FEATURE:
<223> OTHER INFORMATION: synthetic sequence

<400> SEQUENCE: 5

Val Phe Asp Asn Phe Val Leu Lys
1               5


<210> SEQ ID NO 6
<211> LENGTH: 5
<212> TYPE: PRT
<213> ORGANISM: Artificial sequence
```

-continued

<220> FEATURE:
<223> OTHER INFORMATION: synthetic sequence

<400> SEQUENCE: 6

Ile Lys Val Ala Val
1 5

<210> SEQ ID NO 7
<211> LENGTH: 5
<212> TYPE: PRT
<213> ORGANISM: Artificial sequence
<220> FEATURE:
<223> OTHER INFORMATION: synthetic sequence

<400> SEQUENCE: 7

Tyr Ile Gly Ser Arg
1 5

<210> SEQ ID NO 8
<211> LENGTH: 5
<212> TYPE: PRT
<213> ORGANISM: Artificial sequence
<220> FEATURE:
<223> OTHER INFORMATION: synthetic sequence

<400> SEQUENCE: 8

His Ala Val Asp Ile
1 5

<210> SEQ ID NO 9
<211> LENGTH: 10
<212> TYPE: PRT
<213> ORGANISM: Artificial sequence
<220> FEATURE:
<223> OTHER INFORMATION: synthetic sequence

<400> SEQUENCE: 9

His Ala Val Asp Ile His Ala Val Asp Ile
1 5 10

<210> SEQ ID NO 10
<211> LENGTH: 17
<212> TYPE: PRT
<213> ORGANISM: Artificial sequence
<220> FEATURE:
<223> OTHER INFORMATION: synthetic sequence

<400> SEQUENCE: 10

Thr Val Tyr Ala Val Thr Gly Arg Gly Asp Ser Pro Ala Ser Ser Ala
1 5 10 15

Ala

<210> SEQ ID NO 11
<211> LENGTH: 20
<212> TYPE: PRT
<213> ORGANISM: Artificial sequence
<220> FEATURE:
<223> OTHER INFORMATION: synthetic sequence

<400> SEQUENCE: 11

Val Ser Asp Pro Gly Tyr Ile Gly Ser Arg Ser Asp Asp Ser Ala Ser
1 5 10 15

Ala Ser Ala Ala
20

-continued

<210> SEQ ID NO 12
<211> LENGTH: 16
<212> TYPE: PRT
<213> ORGANISM: Artificial sequence
<220> FEATURE:
<223> OTHER INFORMATION: synthetic sequence

<400> SEQUENCE: 12

```
Val Gly Pro Ala Gly Gly Asp Gly Glu Ala Gly Ala Gln Gly Pro Pro
1               5                   10                  15
```

<210> SEQ ID NO 13
<211> LENGTH: 28
<212> TYPE: PRT
<213> ORGANISM: Artificial sequence
<220> FEATURE:
<223> OTHER INFORMATION: synthetic sequence

<400> SEQUENCE: 13

```
Ser Gly Ser Gly Gly Ser Gly Gly Pro Leu Ala Glu Ile Asp Gly Ile
1               5                   10                  15

Glu Leu Thr Tyr Gly Gly Ser Gly Gly Ser Gly Ser
            20                  25
```

<210> SEQ ID NO 14
<211> LENGTH: 26
<212> TYPE: PRT
<213> ORGANISM: Artificial sequence
<220> FEATURE:
<223> OTHER INFORMATION: synthetic sequence

<400> SEQUENCE: 14

```
Ser Gly Ser Gly Gly Ser Gly Gly Leu Asp Val Phe Asp Asn Phe Val
1               5                   10                  15

Leu Lys Gly Gly Ser Gly Gly Ser Gly Ser
            20                  25
```

<210> SEQ ID NO 15
<211> LENGTH: 25
<212> TYPE: PRT
<213> ORGANISM: Artificial sequence
<220> FEATURE:
<223> OTHER INFORMATION: synthetic sequence

<400> SEQUENCE: 15

```
Ser Gly Ser Gly Gly Ser Gly Gly Leu Asp Val Phe Asp Asn Phe Val
1               5                   10                  15

Leu Gly Gly Ser Gly Gly Ser Gly Ser
            20                  25
```

<210> SEQ ID NO 16
<211> LENGTH: 21
<212> TYPE: PRT
<213> ORGANISM: Artificial sequence
<220> FEATURE:
<223> OTHER INFORMATION: synthetic sequence

<400> SEQUENCE: 16

```
Ser Gly Ser Gly Gly Ser Gly Gly His Ala Val Asp Ile Gly Gly Ser
1               5                   10                  15

Gly Gly Ser Gly Ser
            20
```

<210> SEQ ID NO 17
<211> LENGTH: 28

-continued

<212> TYPE: PRT
<213> ORGANISM: Artificial sequence
<220> FEATURE:
<223> OTHER INFORMATION: synthetic sequence

<400> SEQUENCE: 17

Ser Gly Ser Gly Gly Ser Gly Gly His Ala Val Asp Ile Asn Gly His
1 5 10 15

Ala Val Asp Ile Gly Gly Ser Gly Gly Ser Gly Ser
20 25

<210> SEQ ID NO 18
<211> LENGTH: 21
<212> TYPE: PRT
<213> ORGANISM: Artificial sequence
<220> FEATURE:
<223> OTHER INFORMATION: synthetic sequence

<400> SEQUENCE: 18

Ser Gly Ser Gly Gly Ser Gly Gly Ala Asp His Ile Val Gly Gly Ser
1 5 10 15

Gly Gly Ser Gly Ser
20

<210> SEQ ID NO 19
<211> LENGTH: 17
<212> TYPE: PRT
<213> ORGANISM: Artificial sequence
<220> FEATURE:
<223> OTHER INFORMATION: synthetic sequence

<400> SEQUENCE: 19

Thr Val Tyr Ala Val Thr Gly Arg Asp Gly Ser Pro Ala Ser Ser Ala
1 5 10 15

Ala

<210> SEQ ID NO 20
<211> LENGTH: 25
<212> TYPE: PRT
<213> ORGANISM: Artificial sequence
<220> FEATURE:
<223> OTHER INFORMATION: synthetic sequence

<400> SEQUENCE: 20

Val Pro Gly Ile Gly Val Pro Gly Ile Gly Val Pro Gly Lys Gly Val
1 5 10 15

Pro Gly Ile Gly Val Pro Gly Ile Gly
20 25

<210> SEQ ID NO 21
<211> LENGTH: 30
<212> TYPE: PRT
<213> ORGANISM: Artificial sequence
<220> FEATURE:
<223> OTHER INFORMATION: synthetic sequence

<400> SEQUENCE: 21

Val Pro Gly Ile Gly Val Pro Gly Lys Gly Val Pro Gly Tyr Gly Val
1 5 10 15

Pro Gly Ile Gly Val Pro Gly Lys Gly Val Pro Gly Ile Gly
20 25 30

<210> SEQ ID NO 22
<211> LENGTH: 19

-continued

<212> TYPE: PRT
<213> ORGANISM: Artificial sequence
<220> FEATURE:
<223> OTHER INFORMATION: synthetic sequence

<400> SEQUENCE: 22

Ala Arg Lys Gln Ala Ala Ser Ile Lys Val Ala Val Ser Ala Asp Arg
1 5 10 15

Ala Ser Ala

<210> SEQ ID NO 23
<211> LENGTH: 5
<212> TYPE: PRT
<213> ORGANISM: Artificial sequence
<220> FEATURE:
<223> OTHER INFORMATION: synthetic sequence

<400> SEQUENCE: 23

Val Pro Gly Ile Gly
1 5

<210> SEQ ID NO 24
<211> LENGTH: 5
<212> TYPE: PRT
<213> ORGANISM: Artificial sequence
<220> FEATURE:
<223> OTHER INFORMATION: synthetic sequence

<400> SEQUENCE: 24

Val Pro Gly Lys Gly
1 5

<210> SEQ ID NO 25
<211> LENGTH: 5
<212> TYPE: PRT
<213> ORGANISM: Artificial sequence
<220> FEATURE:
<223> OTHER INFORMATION: synthetic sequence

<400> SEQUENCE: 25

Val Pro Gly Tyr Gly
1 5

<210> SEQ ID NO 26
<211> LENGTH: 6
<212> TYPE: PRT
<213> ORGANISM: Artificial sequence
<220> FEATURE:
<223> OTHER INFORMATION: synthetic sequence

<400> SEQUENCE: 26

Val Asp Phe Asn Val Leu
1 5

<210> SEQ ID NO 27
<211> LENGTH: 7
<212> TYPE: PRT
<213> ORGANISM: Artificial sequence
<220> FEATURE:
<223> OTHER INFORMATION: synthetic sequence

<400> SEQUENCE: 27

Val Asp Phe Asn Val Leu Lys
1 5

<210> SEQ ID NO 28

<211> LENGTH: 12
<212> TYPE: PRT
<213> ORGANISM: Artificial sequence
<220> FEATURE:
<223> OTHER INFORMATION: synthetic sequence

<400> SEQUENCE: 28

His Ala Val Asp Ile Asn Gly His Ala Val Asp Ile
1 5 10

<210> SEQ ID NO 29
<211> LENGTH: 5
<212> TYPE: PRT
<213> ORGANISM: Artificial sequence
<220> FEATURE:
<223> OTHER INFORMATION: synthetic sequence

<400> SEQUENCE: 29

Ala Asp His Ile Val
1 5

<210> SEQ ID NO 30
<211> LENGTH: 400
<212> TYPE: PRT
<213> ORGANISM: Artificial sequence
<220> FEATURE:
<223> OTHER INFORMATION: synthetic sequence
<220> FEATURE:
<221> NAME/KEY: SITE
<222> LOCATION: (34)..(34)
<223> OTHER INFORMATION: Xaa is Gly or Asp
<220> FEATURE:
<221> NAME/KEY: SITE
<222> LOCATION: (35)..(35)
<223> OTHER INFORMATION: Xaa is Gly or Asp
<220> FEATURE:
<221> NAME/KEY: SITE
<222> LOCATION: (128)..(128)
<223> OTHER INFORMATION: Xaa is Gly or Asp
<220> FEATURE:
<221> NAME/KEY: SITE
<222> LOCATION: (129)..(129)
<223> OTHER INFORMATION: Xaa is Gly or Asp
<220> FEATURE:
<221> NAME/KEY: SITE
<222> LOCATION: (222)..(222)
<223> OTHER INFORMATION: Xaa is Gly or Asp
<220> FEATURE:
<221> NAME/KEY: SITE
<222> LOCATION: (223)..(223)
<223> OTHER INFORMATION: Xaa is Gly or Asp
<220> FEATURE:
<221> NAME/KEY: SITE
<222> LOCATION: (316)..(316)
<223> OTHER INFORMATION: Xaa is Gly or Asp
<220> FEATURE:
<221> NAME/KEY: SITE
<222> LOCATION: (317)..(317)
<223> OTHER INFORMATION: Xaa is Gly or Asp

<400> SEQUENCE: 30

Met Ala Ser Met Thr Gly Gly Gln Gln His His His His His His Asp
1 5 10 15

Asp Asp Asp Lys Leu Gln Leu Asp Ala Ser Thr Val Tyr Ala Val Gly
20 25 30

Arg Xaa Xaa Ser Pro Ala Ser Ser Ala Val Pro Gly Ile Gly Val Pro
35 40 45

Gly Ile Gly Val Pro Gly Lys Gly Val Pro Gly Ile Gly Val Pro Gly
50 55 60

Ile Gly Val Pro Gly Ile Gly Val Pro Gly Ile Gly Val Pro Gly Lys

-continued

```
65                  70                  75                  80

Gly Val Pro Gly Ile Gly Val Pro Gly Ile Gly Val Pro Gly Ile Gly
                85                  90                  95

Val Pro Gly Ile Gly Val Pro Gly Lys Gly Val Pro Gly Ile Gly Val
            100                 105                 110

Pro Gly Ile Gly Leu Asp Ala Ser Thr Val Tyr Ala Val Gly Arg Xaa
        115                 120                 125

Xaa Ser Pro Ala Ser Ser Ala Val Pro Gly Ile Gly Val Pro Gly Ile
    130                 135                 140

Gly Val Pro Gly Lys Gly Val Pro Gly Ile Gly Val Pro Gly Ile Gly
145                 150                 155                 160

Val Pro Gly Ile Gly Val Pro Gly Ile Gly Val Pro Gly Lys Gly Val
                165                 170                 175

Pro Gly Ile Gly Val Pro Gly Ile Gly Val Pro Gly Ile Gly Val Pro
            180                 185                 190

Gly Ile Gly Val Pro Gly Lys Gly Val Pro Gly Ile Gly Val Pro Gly
        195                 200                 205

Ile Gly Leu Asp Ala Ser Thr Val Tyr Ala Val Gly Arg Xaa Xaa Ser
    210                 215                 220

Pro Ala Ser Ser Ala Val Pro Gly Ile Gly Val Pro Gly Ile Gly Val
225                 230                 235                 240

Pro Gly Lys Gly Val Pro Gly Ile Gly Val Pro Gly Ile Gly Val Pro
                245                 250                 255

Gly Ile Gly Val Pro Gly Ile Gly Val Pro Gly Lys Gly Val Pro Gly
            260                 265                 270

Ile Gly Val Pro Gly Ile Gly Val Pro Gly Ile Gly Val Pro Gly Ile
        275                 280                 285

Gly Val Pro Gly Lys Gly Val Pro Gly Ile Gly Val Pro Gly Ile Gly
    290                 295                 300

Leu Asp Ala Ser Thr Val Tyr Ala Val Gly Arg Xaa Xaa Ser Pro Ala
305                 310                 315                 320

Ser Ser Ala Val Pro Gly Ile Gly Val Pro Gly Ile Gly Val Pro Gly
                325                 330                 335

Lys Gly Val Pro Gly Ile Gly Val Pro Gly Ile Gly Val Pro Gly Ile
            340                 345                 350

Gly Val Pro Gly Ile Gly Val Pro Gly Lys Gly Val Pro Gly Ile Gly
        355                 360                 365

Val Pro Gly Ile Gly Val Pro Gly Ile Gly Val Pro Gly Ile Gly Val
    370                 375                 380

Pro Gly Lys Gly Val Pro Gly Ile Gly Val Pro Gly Ile Gly Leu Glu
385                 390                 395                 400


<210> SEQ ID NO 31
<211> LENGTH: 3
<212> TYPE: PRT
<213> ORGANISM: Artificial sequence
<220> FEATURE:
<223> OTHER INFORMATION: synthetic sequence

<400> SEQUENCE: 31

Arg Gly Asp
1


<210> SEQ ID NO 32
<211> LENGTH: 3
<212> TYPE: PRT
```

<213> ORGANISM: Artificial sequence
<220> FEATURE:
<223> OTHER INFORMATION: synthetic sequence

<400> SEQUENCE: 32

Arg Asp Gly
1

<210> SEQ ID NO 33
<211> LENGTH: 7
<212> TYPE: PRT
<213> ORGANISM: Artificial sequence
<220> FEATURE:
<223> OTHER INFORMATION: synthetic sequence

<400> SEQUENCE: 33

Val Phe Asp Asn Phe Val Leu
1               5

<210> SEQ ID NO 34
<211> LENGTH: 5
<212> TYPE: PRT
<213> ORGANISM: Artificial sequence
<220> FEATURE:
<223> OTHER INFORMATION: synthetic sequence

<400> SEQUENCE: 34

Gly Gly Gly Gly Ser
1               5

<210> SEQ ID NO 35
<211> LENGTH: 14
<212> TYPE: PRT
<213> ORGANISM: Artificial sequence
<220> FEATURE:
<223> OTHER INFORMATION: synthetic sequence

<400> SEQUENCE: 35

Gly Ser Thr Ser Gly Ser Gly Lys Ser Ser Glu Gly Lys Gly
1               5                   10

<210> SEQ ID NO 36
<211> LENGTH: 25
<212> TYPE: PRT
<213> ORGANISM: Artificial sequence
<220> FEATURE:
<223> OTHER INFORMATION: synthetic sequence
<220> FEATURE:
<221> NAME/KEY: SITE
<222> LOCATION: (6)..(10)
<223> OTHER INFORMATION: The amino acids at positions 6 to 10 are either present or absent
<220> FEATURE:
<221> NAME/KEY: SITE
<222> LOCATION: (11)..(15)
<223> OTHER INFORMATION: The amino acids at positions 11 to 15 are either present or absent
<220> FEATURE:
<221> NAME/KEY: SITE
<222> LOCATION: (16)..(20)
<223> OTHER INFORMATION: The amino acids at positions 16 to 20 are either present or absent
<220> FEATURE:
<221> NAME/KEY: SITE
<222> LOCATION: (21)..(25)
<223> OTHER INFORMATION: The amino acids at positions 21 to 25 are either present or absent

<400> SEQUENCE: 36

Gly Gly Gly Gly Ser Gly Gly Gly Gly Ser Gly Gly Gly Gly Ser Gly

```
1               5                   10                  15

Gly Gly Gly Ser Gly Gly Gly Gly Ser
            20                  25
```

<210> SEQ ID NO 37
<211> LENGTH: 19
<212> TYPE: DNA
<213> ORGANISM: Artificial sequence
<220> FEATURE:
<223> OTHER INFORMATION: synthetic sequence

<400> SEQUENCE: 37
ctgagcgccc aagtcaaag 19

<210> SEQ ID NO 38
<211> LENGTH: 19
<212> TYPE: DNA
<213> ORGANISM: Artificial sequence
<220> FEATURE:
<223> OTHER INFORMATION: synthetic sequence

<400> SEQUENCE: 38
gagggcagaa cccgaaacc 19

<210> SEQ ID NO 39
<211> LENGTH: 21
<212> TYPE: DNA
<213> ORGANISM: Artificial sequence
<220> FEATURE:
<223> OTHER INFORMATION: synthetic sequence

<400> SEQUENCE: 39
tcaatagccg ctactggtgt a 21

<210> SEQ ID NO 40
<211> LENGTH: 24
<212> TYPE: DNA
<213> ORGANISM: Artificial sequence
<220> FEATURE:
<223> OTHER INFORMATION: synthetic sequence

<400> SEQUENCE: 40
agaatttact gaaggagctc caag 24

<210> SEQ ID NO 41
<211> LENGTH: 21
<212> TYPE: DNA
<213> ORGANISM: Artificial sequence
<220> FEATURE:
<223> OTHER INFORMATION: synthetic sequence

<400> SEQUENCE: 41
catgtacgtt gctatccagg c 21

<210> SEQ ID NO 42
<211> LENGTH: 21
<212> TYPE: DNA
<213> ORGANISM: Artificial sequence
<220> FEATURE:
<223> OTHER INFORMATION: synthetic sequence

<400> SEQUENCE: 42
agcagtcacc atcgaagaag c 21

<210> SEQ ID NO 43

-continued

```
<211> LENGTH: 21
<212> TYPE: DNA
<213> ORGANISM: Artificial sequence
<220> FEATURE:
<223> OTHER INFORMATION: synthetic sequence

<400> SEQUENCE: 43

ggcgaagttg tagtcgcaga g                                          21


<210> SEQ ID NO 44
<211> LENGTH: 21
<212> TYPE: DNA
<213> ORGANISM: Artificial sequence
<220> FEATURE:
<223> OTHER INFORMATION: synthetic sequence

<400> SEQUENCE: 44

atcacggaca accctctttg c                                          21


<210> SEQ ID NO 45
<211> LENGTH: 24
<212> TYPE: DNA
<213> ORGANISM: Artificial sequence
<220> FEATURE:
<223> OTHER INFORMATION: synthetic sequence

<400> SEQUENCE: 45

tcctctcttt tctccataac atcc                                       24


<210> SEQ ID NO 46
<211> LENGTH: 21
<212> TYPE: DNA
<213> ORGANISM: Artificial sequence
<220> FEATURE:
<223> OTHER INFORMATION: synthetic sequence

<400> SEQUENCE: 46

ctccttaatg tcacgcacga t                                          21
```